United States Patent
Oaks et al.

(10) Patent No.: US 9,931,233 B2
(45) Date of Patent: Apr. 3, 2018

(54) SOFT ORTHOPEDIC KNEE BRACE FOR TREATMENT OF OSTEOARTHRITIS

(75) Inventors: Serena N. Oaks, Encinitas, CA (US); Stefanie L. Mah, El Cajon, CA (US)

(73) Assignee: Breg, Inc., Carlsbad, CA (US)

( * ) Notice: Subject to any disclaimer, the term of this patent is extended or adjusted under 35 U.S.C. 154(b) by 493 days.

(21) Appl. No.: 13/346,658

(22) Filed: Jan. 9, 2012

(65) Prior Publication Data

US 2013/0178772 A1 Jul. 11, 2013

(51) Int. Cl.
*A61F 5/01* (2006.01)

(52) U.S. Cl.
CPC .......... *A61F 5/0109* (2013.01); *A61F 5/0123* (2013.01)

(58) Field of Classification Search
CPC .. A61F 5/37; A61F 5/04; A61F 5/0102; A61F 5/05; A61F 5/0106; A61F 5/0109; A61F 5/0104; A61F 5/05841; A61F 5/05858; A61F 2005/0134; A61F 2005/0137
USPC ............... 128/882; 602/5, 23, 26, 60–63, 16
See application file for complete search history.

(56) References Cited

U.S. PATENT DOCUMENTS

| | | | |
|---|---|---|---|
| 3,669,105 A * | 6/1972 | Castiglia | A61F 5/0125 602/26 |
| 3,804,084 A | 4/1974 | Lehman | |
| 3,817,244 A * | 6/1974 | Taylor | 602/26 |
| 4,240,414 A | 12/1980 | Theisler | |
| 4,353,362 A * | 10/1982 | DeMarco | 602/26 |
| 4,370,978 A | 2/1983 | Palumbo | |
| 4,372,298 A * | 2/1983 | Lerman | A61F 5/0123 602/26 |
| 4,379,463 A | 4/1983 | Meier | |
| 4,381,768 A | 5/1983 | Erichson | |
| 4,423,720 A | 1/1984 | Meier | |
| 4,425,912 A | 1/1984 | Harper | |
| 4,572,170 A | 2/1986 | Cronk | |
| 4,686,969 A | 8/1987 | Scott | |
| 4,724,831 A * | 2/1988 | Huntjens | 602/26 |
| 4,768,500 A | 9/1988 | Mason | |

(Continued)

FOREIGN PATENT DOCUMENTS

| | | | |
|---|---|---|---|
| FR | 2 772 596 | * | 12/1997 |
| WO | WO 2005/120500 A2 | * | 12/2005 |
| WO | 2009052031 A1 | | 4/2009 |

OTHER PUBLICATIONS

Translation, FR 2 772 596.*

(Continued)

*Primary Examiner* — Kari Rodriquez
*Assistant Examiner* — Camtu Nguyen
(74) *Attorney, Agent, or Firm* — Rodney F. Brown

(57) ABSTRACT

An orthopedic knee brace is provided having a sleeve, a longitudinal support assembly and a strapping system. The sleeve is positionable over a knee with the longitudinal support assembly engaging the sleeve. The longitudinal support assembly includes an upper support member, a lower support member and a hinge positionable in engagement with the knee. The strapping system includes a strap extending in a helical path across a lower point on the upper support member proximal to the hinge to an upper point on the upper support member or in a helical path across an upper point on the lower support member proximal to the hinge to a lower point on the lower support member.

30 Claims, 8 Drawing Sheets

(56) References Cited

U.S. PATENT DOCUMENTS

| | | | |
|---|---|---|---|
| 4,791,916 A * | 12/1988 | Paez | A61F 5/0123 602/26 |
| 4,796,610 A | 1/1989 | Cromartie | |
| 4,805,606 A | 2/1989 | McDavid, III | |
| 4,940,045 A | 7/1990 | Cromartie | |
| 5,016,621 A | 5/1991 | Bender | |
| 5,024,216 A * | 6/1991 | Shiono | A61F 5/0123 2/24 |
| 5,086,761 A * | 2/1992 | Ingram | 602/26 |
| 5,131,385 A | 7/1992 | Kuehnegger | |
| 5,133,341 A | 7/1992 | Singer | |
| 5,139,476 A | 8/1992 | Peters | |
| 5,139,477 A | 8/1992 | Peters | |
| 5,221,252 A | 6/1993 | Caprio, Jr. | |
| 5,277,697 A * | 1/1994 | France | A61F 5/0125 602/16 |
| 5,277,698 A * | 1/1994 | Taylor | A61F 5/0123 602/26 |
| 5,399,153 A | 3/1995 | Caprio, Jr. | |
| 5,417,646 A | 5/1995 | Gauvry | |
| 5,458,565 A | 10/1995 | Tillinghast, III | |
| 5,472,413 A * | 12/1995 | Detty | A61F 5/0104 2/16 |
| 5,512,039 A | 4/1996 | White | |
| 5,513,658 A | 5/1996 | Goseki | |
| 5,582,584 A | 12/1996 | Billotti | |
| 5,599,288 A * | 2/1997 | Shirley | A61F 5/0123 602/16 |
| 5,649,901 A | 7/1997 | Dipietro | |
| 5,656,023 A | 8/1997 | Caprio, Jr. | |
| 5,759,167 A * | 6/1998 | Shields, Jr. | A61F 5/0106 602/26 |
| 5,797,864 A * | 8/1998 | Taylor | A61F 5/0109 602/26 |
| 5,807,294 A | 9/1998 | Cawley | |
| 5,823,931 A | 10/1998 | Gilmour | |
| 5,857,989 A | 1/1999 | Smith, III | |
| 5,865,777 A * | 2/1999 | Detty | 602/26 |
| 5,873,848 A * | 2/1999 | Fulkerson | A61F 5/0106 602/26 |
| 6,010,474 A * | 1/2000 | Wycoki | A61F 5/0102 602/23 |
| 6,063,046 A | 5/2000 | Bodenschatz | |
| 6,287,268 B1 | 9/2001 | Gilmour | |
| 6,436,066 B1 | 8/2002 | Lockhart | |
| 6,852,088 B2 | 2/2005 | Gaylord | |
| 6,994,682 B2 | 2/2006 | Bauerfeind | |
| 7,004,919 B2 | 2/2006 | Gaylord | |
| 7,198,610 B2 | 4/2007 | Ingimundarsun | |
| 7,264,605 B2 | 9/2007 | Gaylord | |
| 7,393,336 B2 | 7/2008 | Sloot | |
| 7,594,897 B2 * | 9/2009 | Koby | A41D 13/065 128/882 |
| 7,597,675 B2 | 10/2009 | Ingimundarsun | |
| 7,625,350 B2 | 12/2009 | Hunter | |
| 7,713,225 B2 | 5/2010 | Ingimundarsun | |
| 7,749,181 B2 | 6/2010 | Simmons | |
| 7,794,418 B2 | 9/2010 | Ingimundarsun | |
| 7,862,528 B2 | 1/2011 | Scott | |
| 7,867,183 B2 | 1/2011 | Kazmierczak | |
| 7,896,827 B2 | 3/2011 | Ingimundarsun | |
| 7,905,851 B1 | 3/2011 | Bledsoe | |
| 7,914,475 B2 | 3/2011 | Wyatt | |
| 7,959,590 B2 | 6/2011 | Scott | |
| 8,328,747 B2 * | 12/2012 | Matsunaga | 602/26 |
| 2005/0038367 A1 | 2/2005 | McCormick | |
| 2007/0167895 A1 | 7/2007 | Gramza | |
| 2011/0319800 A1 * | 12/2011 | Matsunaga | A61F 5/0106 602/16 |

OTHER PUBLICATIONS

Partial European Search Report from corresponding European patent application, excerpted pp. 1-2, published in EPO Sep. 4, 2013.

* cited by examiner

SOFT ORTHOPEDIC KNEE BRACE FOR TREATMENT OF OSTEOARTHRITIS

BACKGROUND OF THE INVENTION

The present invention relates generally to orthopedic braces, and more particularly to an orthopedic knee brace.

Orthopedic braces embody a broad range of apparatuses, each having the common purpose of supporting and/or stabilizing a skeletal joint when worn on the body of a user. The orthopedic brace may serve either a preventative role or a remedial role. In a preventative role, the brace provides added support and stability to a healthy skeletal joint, thereby reducing the risk of injury when the joint is subjected to undue stress. In a remedial role, the brace supports and stabilizes a skeletal joint which has been weakened by injury or other infirmity, thereby reinforcing the joint and reducing the risk of further injury while the joint is rehabilitated.

Conventional orthopedic knee braces may be generally characterized as either frame braces or soft braces. As the name implies, a conventional frame brace has a frame which is secured to the leg by a plurality of straps engaging the frame and circumscribing the leg. The frame typically includes two rotationally-jointed longitudinal supports positioned on opposing sides of the leg. As such, one longitudinal support engages the medial side of the leg at the affected knee to be stabilized as well as the upper and lower leg above and below the affected knee, respectively. The other longitudinal support correspondingly engages the lateral side of the leg.

Each longitudinal support consists of a pair of relatively rigid upper and lower arms and a hinge which rotationally interconnects the upper and lower arms to one another. The upper and lower arms are positioned adjacent to the upper and lower leg, respectively, while the hinge is positioned adjacent to the knee. The frame may also include arcuate-shaped upper and lower cuffs. The upper cuff may be attached to the medial and lateral upper arms and extend therebetween engaging the anterior or posterior face of the upper leg, while the lower cuff may correspondingly be attached to the medial and lateral lower arms and likewise extend therebetween engaging the anterior or posterior face of the lower leg. In a common alternate configuration of the frame, one longitudinal support is omitted from the frame so that only one side of the leg, either the medial or lateral side, is engaged by a longitudinal support. In any case, the frame brace diverts a substantial fraction of the dynamic and static force loads from the knee to the rigid frame, thereby supporting and stabilizing the knee.

A conventional soft brace differs from a frame brace insofar as the soft brace has a compression sleeve which is formed from a pliant material, which wraps around the leg at the knee forming a tube-like structure. The sleeve encloses the knee and a portion of the upper and lower legs adjacent to the knee. The relatively tightly-wrapped sleeve of the soft brace applies radial compression to the knee, thereby supporting and stabilizing the knee. The soft brace may also have one or more straps which engage the sleeve and circumscribe the leg to increase the radially-directed compressive force on the knee. The support and stabilizing function of the soft brace may be further enhanced by incorporating rigid or semi-rigid stays into the sleeve.

One destabilizing condition of the knee joint which can be mitigated by use of a knee brace is osteoarthritis. Knee osteoarthritis is a degenerative disease that results in chronic pain to the subject when the knee is statically or dynamically loaded. Osteoarthritis is commonly the result of aging, joint overuse, or injury. Uni-compartmental osteoarthritic knee pain is caused by an unbalanced loading on the medial or lateral compartment of the knee which closes the clearance space forming the compartment between the condyles of the femur and tibia. When there is contact of the condyles in the afflicted compartment of the knee, abrasion occurs at the contact surface producing pain in the joint.

A number of frame-type knee braces are specifically designed to noninvasively treat osteoarthritis by applying a corrective force to the knee of the user, such as the knee braces disclosed in U.S. Pat. Nos. 5,277,698; 5,458,565 and 5,807,294. If a user's osteoarthritis is caused by overloading the medial compartment of the knee, the frame of these exemplary knee braces is provided with a lateral longitudinal support which exerts a linear biasing force on the knee in the medial direction to reduce the load on the medial compartment. Conversely, if a user's osteoarthritis is caused by overloading the lateral compartment of the knee, the frame is provided with a medial longitudinal support which exerts a linear biasing force on the knee in the lateral direction to reduce the load on the lateral compartment.

The present invention recognizes the need for a soft-type knee brace which has an effective osteoarthritic treatment function. Accordingly, it is generally an object of the present invention to provide a soft brace which satisfies the above-recited need. This object and others are accomplished in accordance with the invention described hereafter.

SUMMARY OF THE INVENTION

The present invention is characterized as a knee brace comprising a sleeve, a body tension tab, and a flap tension tab. The sleeve is wrappable around a knee in an operative configuration adapted to enclose a knee of a leg of a wearer when the sleeve is worn on the leg of the wearer. The sleeve includes an outer body and an inner flap attached to the body. The body tension tab extends from the body and has a body releasable tab fastener enabling releasable fastening of the body tension tab to the sleeve when the sleeve is wrapped around the knee. The flap tension tab extends from the flap and has a flap releasable tab fastener enabling releasable fastening of the flap tension tab to the sleeve when the sleeve is wrapped around the knee. The body tension tab is preferably narrower than the body and the flap tension tab is preferably narrower than the flap.

In accordance with an embodiment of the present invention, the body has a first body edge and an opposing second body edge. The flap has a first flap edge and an opposing second flap edge and the first flap edge is attached to the body proximal to the second body edge. The body tension tab extends from the second body edge and the body releasable tab fastener enables releasable fastening of the body tension tab to the sleeve at the first body edge when the sleeve is wrapped around the knee. The flap tension tab extends from the second flap edge and the flap releasable tab fastener enables releasable fastening of the flap tension tab to the sleeve at the first body edge when the sleeve is wrapped around the knee.

In accordance with another embodiment of the present invention, the body tension tab is a first body tension tab and the body releasable tab fastener is a first body releasable tab fastener. The knee brace further comprises a second body tension tab extending from the body and having a second body releasable tab fastener. The second body releasable tab fastener enables releasable fastening of the second body tension tab to the sleeve when the sleeve is wrapped around the knee with the first body tension tab positionable above the knee and the second body tension tab is positionable below the knee.

In accordance with yet another embodiment of the present invention, the flap tension tab is a first flap tension tab and the flap releasable tab fastener is a first flap releasable tab fastener. The knee brace further comprises a second flap tension tab extending from the flap and having a second flap releasable tab fastener. The second flap releasable tab fastener enables releasable fastening of the second flap tension tab to the sleeve when the sleeve is wrapped around the knee with the first flap tension tab is positionable above the knee and the second flap tension tab is positionable below the knee. In addition the first flap tension tab is preferably positioned between the first body tension tab and the second flap tension tab and the second flap tension tab is preferably positioned between the first flap tension tab and the second body tension tab when the sleeve is wrapped around the knee.

In accordance with another embodiment of the present invention, the knee brace comprises a finger pull on one or more of the tension tabs. The finger pull is an opening between the tension tab and a segment of material overlaying the tension tab sized to receive one or more fingertips.

The present invention is alternately characterized as a knee brace comprising a sleeve, a longitudinal support assembly and a strapping system. The sleeve is positionable over a knee with the longitudinal support assembly engaging the sleeve. The longitudinal support assembly includes an upper support member, a lower support member and a hinge positionable in engagement with the knee. The strapping system includes an upper strap extending in a helical path across a lower point on the upper support member proximal to the hinge to an upper point on the upper support member.

In accordance with one embodiment, the upper strap has first and second upper strap ends, the second upper strap end is attached to the sleeve adjacent to the lower point on the upper support member and the first upper strap end is releasably attached to the upper point on the upper support member. Releasable attachment of the first upper strap end to the upper point on the upper support member is preferably effected by threading the first upper strap end through an upper strap retainer mounted on the upper support member at the upper point. The knee brace also preferably further comprises an upper pocket associated with the sleeve which retains the upper support member.

In accordance with another embodiment, the strapping system includes a lower strap extending in a helical path across an upper point on the lower support member proximal to the hinge to a lower point on the lower support member. In accordance with yet another embodiment, the lower strap has first and second lower strap ends, the second lower strap end is attached to the sleeve adjacent to the upper point on the lower support member and the first lower strap end is releasably attached to the lower point on the lower support member. Releasable attachment of the first lower strap end to the upper point on the lower support member is preferably effected by threading the first lower strap end through a lower strap retainer mounted on the lower support member at the lower point. The knee brace also preferably further comprises a lower pocket associated with the sleeve retaining the lower support member.

In accordance with another embodiment, the sleeve has a substantially permanent tube-like configuration and is positionable over the knee by sliding the sleeve from the foot up the leg. Alternatively, the sleeve has first and second edges and is positionable over the knee by wrapping the sleeve around the knee and releasably joining the first and second edges. The second edge of the sleeve preferably has a tension tab extending therefrom. The first and second edges are releasably joined together by releasably fastening the tension tab of the second edge to an outer face of the sleeve at the first edge.

The present invention is alternately characterized as a knee brace comprising a sleeve, a body tension tab, a flap tension tab, a longitudinal support assembly and a strapping system. The sleeve is wrappable around a knee and includes a body and a flap attached to the body. The body tension tab extends from the body and has a body releasable tab fastener enabling releasable fastening of the body tension tab to the sleeve when the sleeve is wrapped around the knee. The flap tension tab extends from the flap and has a flap releasable tab fastener enabling releasable fastening of the flap tension tab to the sleeve when the sleeve is wrapped around the knee. The longitudinal support assembly engages the sleeve and includes an upper support member, a lower support member and a hinge positionable in engagement with the knee. The strapping system includes a strap extending in a helical path across a lower point on the upper support member proximal to the hinge to an upper point on the upper support member or in a helical path across an upper point on the lower support member proximal to the hinge to a lower point on the lower support member.

The present invention is alternately characterized as a knee brace comprising a sleeve wrappable around a knee, a tension tab having a releasable tab fastener, and a finger pull positioned on the tension tab. The releasable tab fastener enables releasable fastening of the tension tab to the sleeve when the sleeve is wrapped around the knee. The finger pull is an opening between the tension tab and a segment of material overlaying the tension tab sized to receive one or more fingertips and facilitate tensioning the sleeve.

The present invention will be further understood from the drawings and the following detailed description.

DESCRIPTION OF PREFERRED EMBODIMENTS

Figure 1:
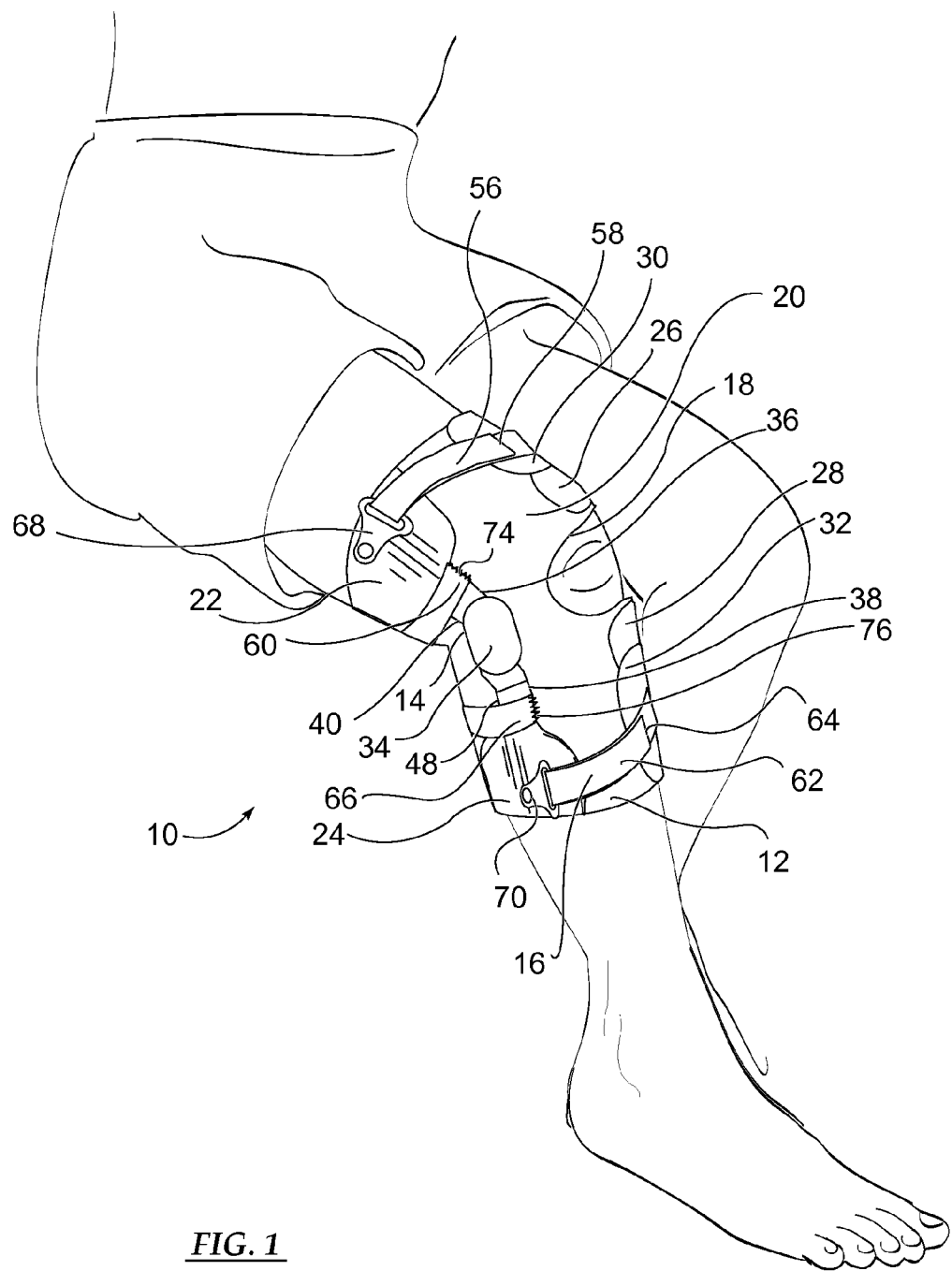
FIG. 1 is a perspective view of an orthopedic knee brace of the present invention worn on the leg of a user.

Referring to FIG. 1, an orthopedic knee brace of the present invention is shown worn on the leg of a user and generally designated 10. For purposes of illustration, the knee brace 10 is configured to be worn on the right leg of the user for stabilizing the right knee. However, it is readily apparent to one of ordinary skill in the art from the teaching herein that the knee brace of the present invention can readily be adapted for wearing on the left leg of a user for stabilizing the left knee.

The knee brace 10 comprises a sleeve 12, a longitudinal support assembly 14 integral with the sleeve 12, and an associated strapping system 16 likewise integral with the sleeve 12. The knee brace 10 and correspondingly the sleeve 12 are positioned over the knee of the user as well as over the adjacent portions of the upper and lower leg. The sleeve 12 substantially encloses the knee and the adjacent portions of the upper and lower leg with the exception of a patellar opening 18 formed in the sleeve 12 which exposes the patella when the knee brace 10 is worn by the user. The sleeve 12 comprises a main body 20, upper and lower cuff pockets 22, 24, upper and lower inner tension tabs 26, 28, and upper and lower outer tension tabs 30, 32. The sleeve 12 is preferably constructed from an elastically stretchable sheet of pliant fabric, foam, combination thereof, or the like. Alternatively, the sleeve can be constructed from a substantially non-stretchable pliant material.

The longitudinal support assembly is not limited to any one configuration. Any number of longitudinal support assemblies well known in the prior art have utility in the knee brace 10 of the present invention. Nevertheless, a preferred embodiment of a longitudinal support assembly having utility herein is shown in FIG. 1 positioned alongside the lateral side of the leg in a substantially vertical orientation. The longitudinal support assembly 14 comprises a rotational hinge 34, an upper support member 36, and a lower support member 38. The rotational hinge 34 is a conventional orthopedic knee brace hinge many of which are well known in the art. The rotational hinge is preferably substantially inflexible and is positioned to engage the lateral side of the knee. Each support member 36, 38 has a substantially similar construction and configuration as the other. The upper support member 36 is positioned alongside and engages the lateral side of the upper leg above the knee, while the lower support member 38 is positioned alongside and engages the lateral side of the lower leg below the knee.

Figure 2:
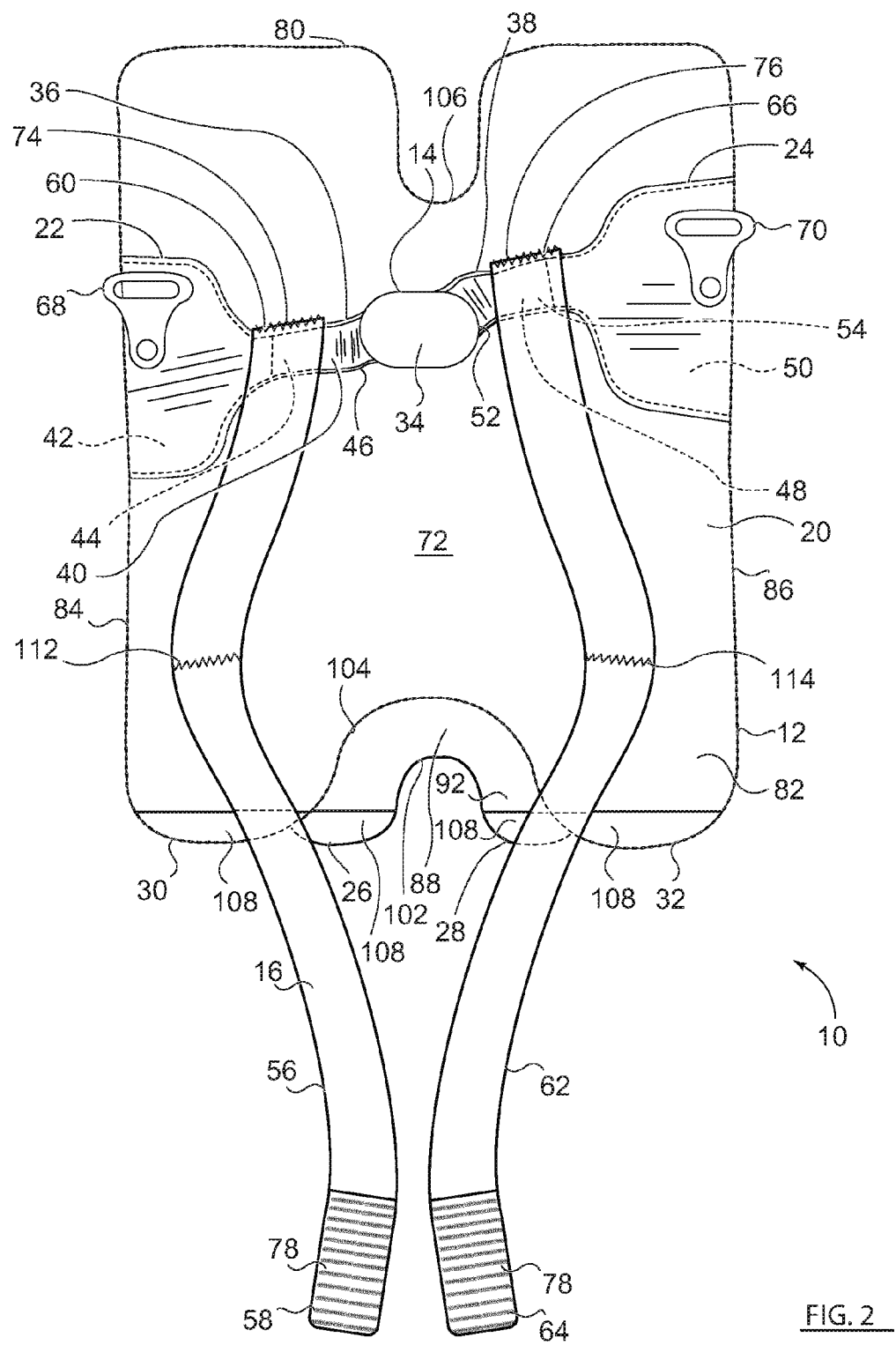
FIG. 2 is a front view of the orthopedic knee brace of FIG. 1 laid out flat off the leg of the user.
Figure 3:
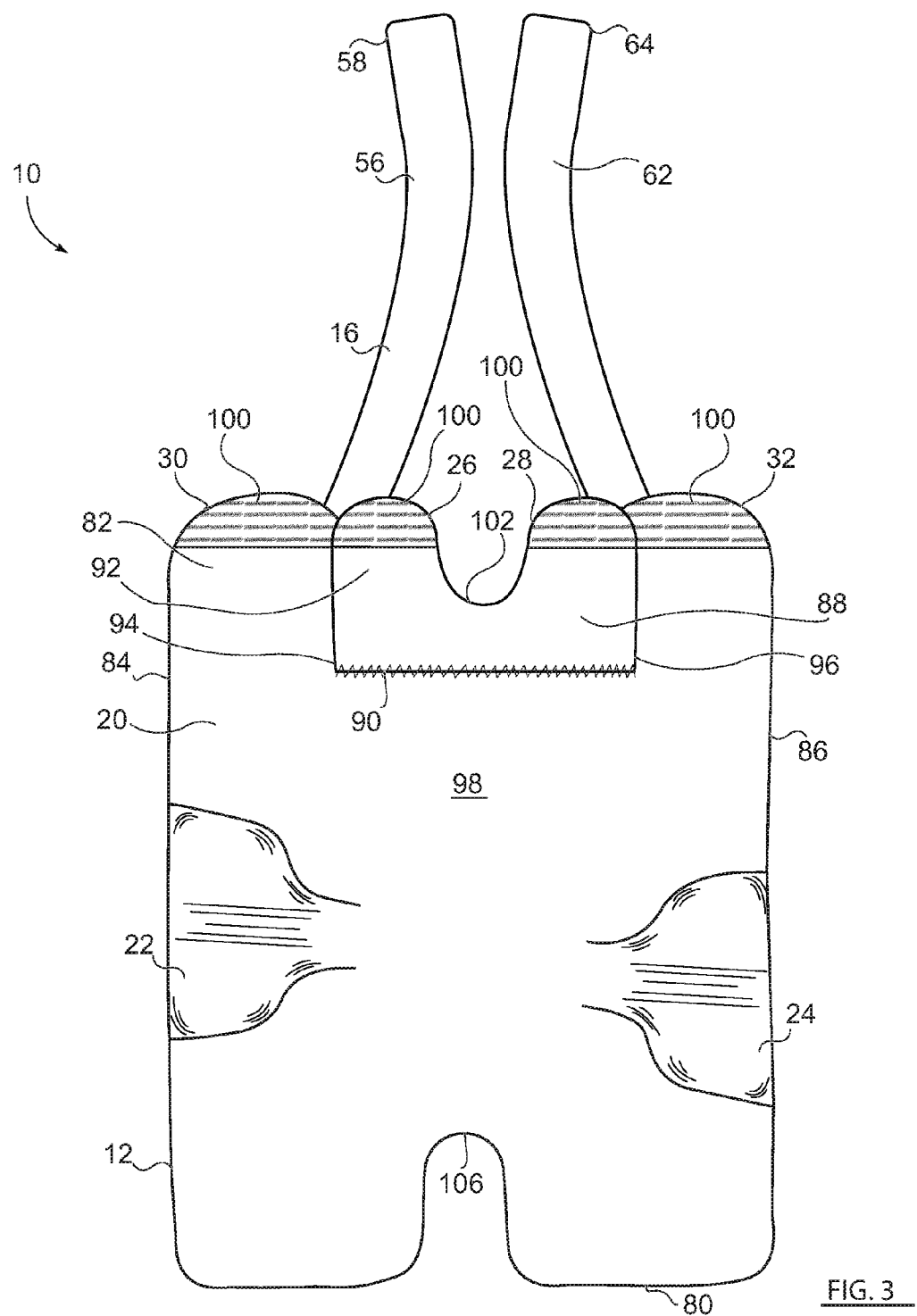
FIG. 3 is a rear view of the orthopedic knee brace of FIG. 1 laid out flat off the leg of the user.

Referring additionally to FIGS. 2 and 3, wherein like reference characters indicate the same or similar elements as in FIG. 1, a preferred upper support member 36 comprises an upper arm 40 and an upper cuff 42. The upper arm 40 has a vertically-aligned elongate configuration with an upper end 44 and a lower end 46. The lower end 46 rotatably extends from the upper end of the rotational hinge 34, while the upper end 44 is preferably stationarily and permanently attached to or integral with the upper cuff 42. The upper arm 40 has a relatively flat straight configuration, although it is preferably bowed slightly outward at its lower end 46 proximal to the rotational hinge 34 to avoid contact with the knee when the knee brace 10 is worn by the user. The upper cuff 42 has an expanded arcuate concave surface configured to conform to and engage the surface contour of the lateral side of the upper leg adjacent to the knee. The upper cuff pocket 22 and upper cuff 42 are correspondingly sized and configured so that the upper cuff 42 can be received and retained within the upper cuff pocket 22.

A preferred lower support member 38 similarly comprises a lower arm 48 and a lower cuff 50. The lower arm 48 likewise has a vertically-aligned elongate configuration with an upper end 52 and a lower end 54. The upper end 52 rotatably extends from the lower end of the rotational hinge 34, while the lower end 54 is preferably stationarily and permanently attached to or integral with the lower cuff 50. The lower arm 48 has a relatively flat straight configuration, although it is preferably bowed slightly outward at its upper end 52 proximal to the rotational hinge 34 to avoid contact with the knee. The lower cuff 50 likewise has an expanded arcuate concave surface configured to conform to and engage the surface contour of the lateral side of the lower leg adjacent to the knee. The lower cuff pocket 24 and lower cuff 50 are correspondingly sized and configured so that the lower cuff 50 can be received and retained within the lower cuff pocket 24. Retention of the upper and lower cuffs 42, 50 within the upper and lower cuff pockets 22, 24, respectively, effectively merges the longitudinal support assembly 14 and sleeve 12 into a unitary integral structure. It is noted that the terms "engaged" and "engagement" are used herein with reference to the spatial relation between the longitudinal support assembly 14 and the leg of the user wearing the knee brace 10. The terms "engaged" and "engagement" encompass the case where the longitudinal support assembly 14 directly contacts the leg of the user as well as the case where the longitudinal support assembly 14 abuts or rests against the leg of the user, but with the sleeve 12 or some other pliant padding intervening between them.

In accordance with the present configuration of the knee brace 10, the upper support member 36, including the upper arm 40 and stationarily-attached upper cuff 42, is rotatable in unison about the rotational hinge 34 above the knee. The lower support member 38, including the lower arm 48 and stationarily-attached lower cuff 50, is likewise rotatable in unison about the rotational hinge 34 below the knee. The sleeve 12 is sufficiently flexible that it does not substantially impede rotation of the upper support member 36 or the lower support member 38 relative to the rotational hinge 34 as they correspondingly track the movement of the knee across its desired range of motion.

The upper and lower arms 40, 48 are preferably formed from a rigid or semi-rigid metal, while the upper and lower cuffs 42, 50 are preferably formed from a rigid or semi-rigid plastic. Nevertheless, the upper and lower arms 40, 48 can alternatively be formed from a rigid or semi-rigid plastic, fiberglass, composite, combination thereof, or the like. The upper and lower cuffs 42, 50 can alternatively be formed from a rigid or semi-rigid metal, fiberglass, composite, combination thereof, or the like. In any case, the upper and lower support members 36, 38 having the above-recited construction are deemed substantially rigid relative to the sleeve 12 for purposes of the present description although the upper and lower support members 36, 38 may have some flex to them.

The strapping system of the present invention is likewise not limited to any one configuration. Nevertheless, a preferred embodiment of a strapping system having utility herein is shown in FIGS. 1-3 and designated 16. The strapping system 16 comprises a pair of straps, namely, an upper strap 56 having a first end 58 and a second end 60 and a lower strap 62 similarly having a first end 64 and a second end 66. The strapping system 16 further comprises a pair of strap retainers, namely, an upper strap retainer 68 associated with the first end 58 of the upper strap 56 and a lower strap retainer 70 associated with the first end 64 of the lower strap 62. The upper and lower straps 56, 62 are each flexible, yet relatively non-stretchable, straps, preferably constructed from cloth or the like. The second end 60 of the upper strap 56 is preferably permanently attached to the outer face 72 of the sleeve 12 at the anterior edge of the upper arm 40 proximal to the upper end of the rotational hinge 34 by sewing or other attachment means to form an upper union 74, such as a seam, where the second end 60 and sleeve 12 attach to one another. In contrast, the first end 58 of the upper strap 56 preferably remains detached from the sleeve 12 when the knee brace 10 is off the leg as shown in FIGS. 2 and 3. The second end 66 of the lower strap 62 is similarly preferably permanently attached to the outer face 72 of the sleeve 12 at the anterior edge of the lower arm 48 proximal to the lower end of the rotational hinge 34 by sewing or other attachment means to form a lower union 76, while the first end 64 of the lower strap 62 preferably remains detached from the sleeve 12 when the knee brace 10 is off the leg. Although not shown, the second end 60 of the upper strap 56 can alternatively be attached to the anterior edge of the upper arm 40 and the second end 66 of the lower strap 62 can alternatively be attached to the anterior edge of the lower arm 48.

The free first ends 58, 64 of the upper and lower straps 56, 62, respectively, are each preferably provided with a releasable fastener 78. A preferred releasable fastener 78 is the hook or loop material of a hook-and-loop fastener commonly known by the trade name VELCRO. In the present embodiment, a patch of hook material is permanently attached to the first ends 58, 64 of the upper and lower straps 56, 62, respectively, by sewing or the like while the outer face of the body of the upper and lower straps 56, 62 is preferably continuously covered with, or integrally formed from, loop material. This enables the user to adjust the length and tension of the upper and lower straps 56, 62 to a desired length and tension in a manner described below.

The upper strap 56 is a circumferential strap having a spiral or helical path extending around the upper leg. In particular, the upper strap 56 first extends diagonally upwardly from its fixed second end 60 at the upper union 74 posteriorly across the outer face of the upper arm 40, around the upper leg and continues extending diagonally upwardly, but anteriorly around the upper leg across the upper cuff 42 to the upper strap retainer 68 which is coextensively positioned with the upper cuff 42 and upper cuff pocket 22 of the sleeve 12. The upper strap retainer 68 includes a strap loop and is preferably permanently rotatably fastened to the upper cuff 42 by a conventional fastener such as a rivet. In sum, the upper strap 56 extends from the upper union 74 across a lower point on the upper support member 36 and helically to an upper point on the upper support member 36 coinciding with the upper strap retainer 68 where the upper strap 56 is releasably attached thereto.

The lower strap 62 is similarly a circumferential strap having a spiral or helical path extending around the lower leg. In particular, the lower strap 62 first extends diagonally downwardly from its fixed second end 66 at the lower union 76 posteriorly across the outer face of the lower arm 48, around the lower leg and continues extending diagonally downwardly, but anteriorly around the lower leg across the lower cuff 50 to the lower strap retainer 70 which is coextensively positioned with the lower cuff 50 and lower cuff pocket 24 of the sleeve 12. The lower strap retainer 70 likewise includes a strap loop and is preferably permanently rotatably fastened to the lower cuff 50. In sum, the lower strap 62 extends from the upper union 76 across an upper point on the lower support member 38 and helically to a lower point on the lower support member 38 coinciding with the lower strap retainer 70 where the lower strap 62 is releasably attached thereto.

When the sleeve 12 is laid out flat off of the leg in an inoperative configuration as shown in FIGS. 2 and 3, the main body 20 of the sleeve 12 has an approximately rectangular configuration with opposing substantially vertical edges 80, 82 and opposing upper and lower substantially horizontal edges 84, 86. Although not shown, the substantially vertical edges 80, 82 of the sleeve 12 may have a somewhat downward taper in correspondence to the downward taper of the leg so that the sleeve 12 can be more readily conformed to the contour of the leg when the knee brace 10 is being mounted on the leg in a manner described below. In any case, the upper and lower inner tension tabs 26, 28 and upper and lower outer tension tabs 30, 32 are all positioned proximal to the edge 82 of the main body 20.

The proximal position of the upper and lower outer tension tabs 30, 32 to the edge 82 of the main body 20 is effected by integrating the tabs 30, 32 with the edge 82 and extending the tabs 30, 32 directly therefrom. Although also positioned proximal to the edge 82, the upper and lower inner tension tabs 26, 28 are not attached to or integral with the edge 82, but are connected to the sleeve 12 by means of an inner tab flap 88. The inner tab flap 88 is preferably constructed from substantially the same material as the remainder of the sleeve 12 and likewise has an approximately rectangular configuration with opposing inner and outer substantially vertical edges 90, 92 and opposing upper and lower substantially horizontal edges 94, 96. The upper and lower inner tension tabs 26, 28 extend directly from and are integral with the outer edge 92 of the inner tab flap 88. The inner edge 90 of the inner tab flap 88 is preferably permanently attached to the inner face 98 of the sleeve 12 between the edges 80, 82, but more proximal to the edge 82, by sewing or other attachment means to form a union such as a seam, about which the inner tab flap 88 is pivotable. As such, the inner tab flap 88 effectively connects the upper and lower inner tension tabs 26, 28 to the sleeve 12. The remaining edges 92, 94, 96 of the inner tab flap 88 are free and unattached to the sleeve 12.

The upper and lower inner tension tabs 26, 28 and upper and lower outer tension tabs 30, 32 each have an approximately hemispherical configuration. The upper inner tension tab 28 and upper outer tension tab 30 are preferably sized and positioned relative to one another such that they partially overlap one another when the knee brace 10 is laid out flat. The lower inner tension tab 30 and lower outer tension tab 32 are likewise preferably sized and positioned relative to one another such that they partially overlap one another. All of the inner faces of the tension tabs 26, 28, 30, 32 are each preferably provided with a releasable fastener 100. A preferred releasable fastener 100 is the hook or loop material of a hook-and-loop fastener. In the present embodiment, a patch of hook material is permanently attached to the inner faces of the tension tabs 26, 28, 30, 32 as shown in FIG. 2 by sewing or other attachment means while the outer face 72 of the sleeve 12 proximal to the edge 80 as shown in FIG. 3 is preferably continuously covered with, or integrally formed from, loop material. This enables the user to releasably fasten the inner faces of the tension tabs 26, 28, 30, 32 to the outer face 72 of the sleeve 12 proximal to its edge 80, thereby forming a tube-like configuration when the knee brace 10 is worn on the leg as shown in FIG. 1 or when being mounted on the leg in a manner described below with additional reference to FIGS. 5-8.

The upper and lower inner tension tabs 26, 28 are separated from one another along the outer edge 92 of the inner tab flap 88 by an intervening indentation 102 formed in the outer edge 92. The indentation 102 aligns with a corresponding indentation 104 formed in the edge 82 of the main body 20 of the sleeve 12 between the upper and lower outer tension tabs 30, 32. When the knee brace 10 is configured in a tube-like manner for wearing on the leg as shown in FIG. 1, indentations 102, 104 also align with a corresponding indentation 106 formed in the opposing edge 80 of the main body 20 of the sleeve 12, thereby providing the patellar opening 18 in the sleeve 12.

Figure 4:
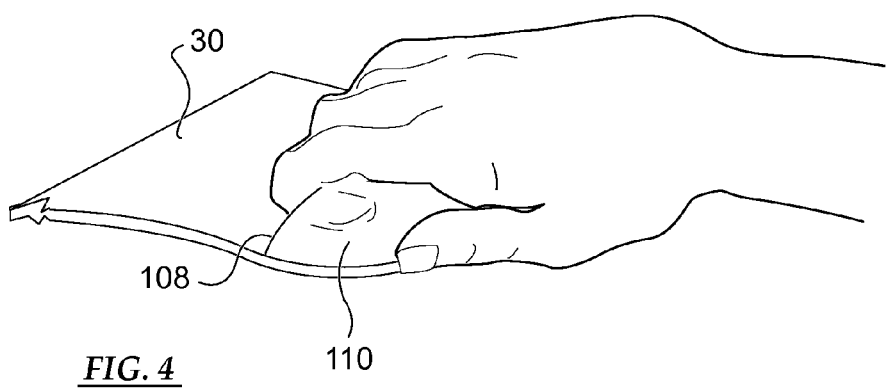
FIG. 4 is a close-up perspective view showing use of a finger pull on a tension tab employed on the orthopedic knee brace of FIG. 1

All of the outer faces of the tension tabs 26, 28, 30, 32 are each preferably provided with a finger pull 108 as shown in FIGS. 1 and 3 and additionally with reference to FIG. 4. The finger pull 108 preferably includes a segment 110 of stretchable pliant material sized and configured in correspondence with the end of each tension tab 26, 28, 30, 32. The segment 110 overlays the end of each tension tab 26, 28, 30, 32 and is permanently attached thereto by sewing or other attachment means, but only along its arcuate outer periphery, while remaining unattached and open along its straight inner periphery. As such, the finger pull 108 constitutes an open pocket formed at the end of each tension tab 26, 28, 30, 32. The finger pull 108 enables the user to firmly grip the tension tab 26, 28, 30, 32 by inserting one or more fingertips into the opening along the straight inner periphery between the segment 110 and tension tab 26, 28, 30, 32 as shown in FIG. 4 and exert a substantial pulling force on the tension tab 26, 28, 30, 32 when tensioning the sleeve 12 in a manner described below.

Referring back to FIG. 2, the strapping system 16 preferably further comprises a pair of upper and lower strap attachments 112, 114 which permanently attach the upper and lower straps 56, 62 to the outer face 72 of the sleeve 12. The upper and lower strap attachments 112, 114 are preferably positioned at selected points mid-length on the upper and lower straps 56, 62, respectively, and at selected points on the outer face 72 of the sleeve 12 which align with to the medial side of the leg when the knee brace 10 is worn on the leg as shown in FIG. 1. The upper and lower strap attachments 112, 114 can simply be a seam effected by sewing or otherwise affixing the upper and lower straps 56, 62 directly to the outer face 72 of the sleeve 12 at the selected points. Alternatively, the upper and lower strap attachments 112, 114 can be effected by sewing or otherwise affixing two ends of a cloth loop (not shown) to the inner face of each strap 56, 62 at the selected point and sewing or otherwise affixing two ends of a corresponding cloth loop (not shown) to the outer face 72 of the sleeve 12 at the selected point such that the cloth loops pass through one another and anchor the upper and lower straps 56, 62 to the outer face 72 of the sleeve 12 at the location of the upper and lower strap attachments 112, 114, respectively. In yet another alternative, the upper and lower strap attachments 112, 114 can be effected by sewing or otherwise affixing one end of a single cloth segment (not shown) to the inner face of each strap 56, 62 at the selected point and sewing or otherwise affixing the opposite end of the cloth segment to the outer face 72 of the sleeve 12 at the selected point such that the cloth segment anchors the upper and lower straps 56, 62 to the outer face 72 of the sleeve 12 at the location of the upper and lower strap attachments 112, 114, respectively.

Figure 5:
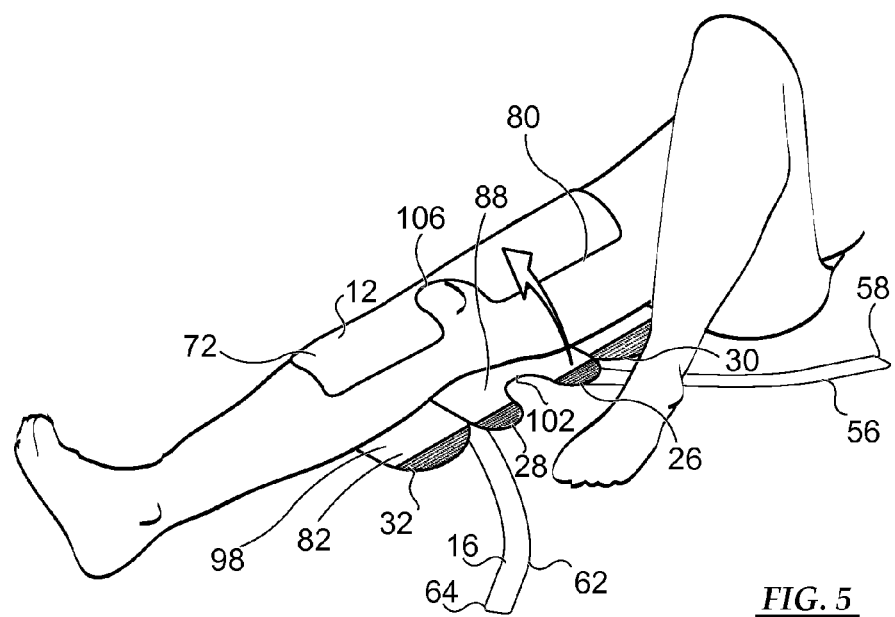
FIGS. 5-11 demonstrate a method for mounting the orthopedic knee brace of FIG. 1 on the leg of the user.
Figure 6:
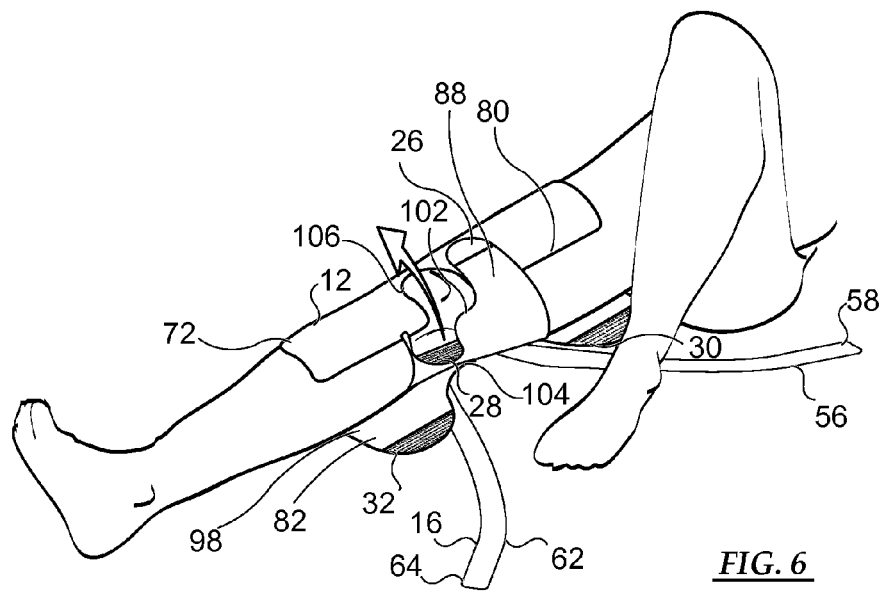
Figure 7:
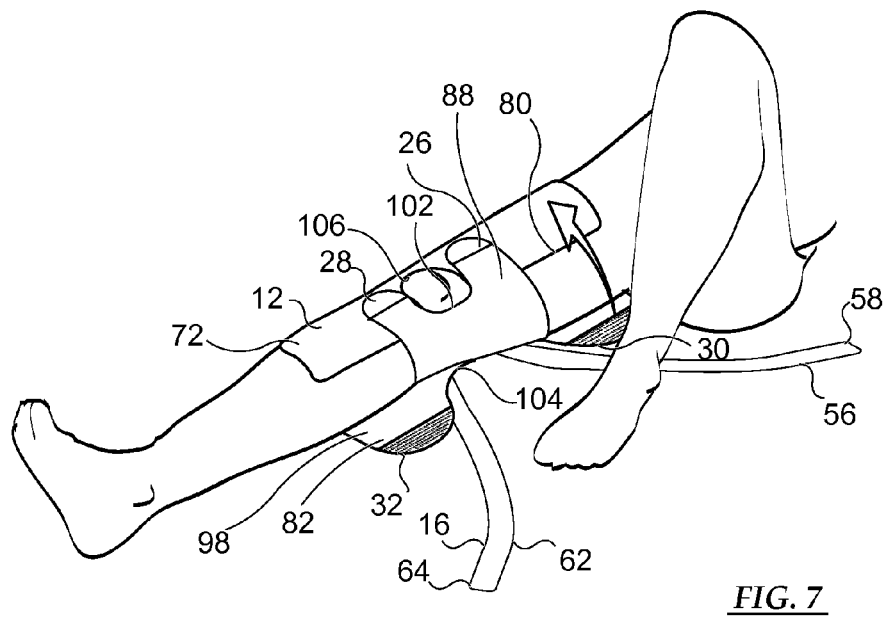

A method for mounting the knee brace 10 on the leg of the user is described hereafter with reference to FIGS. 5-11. Referring initially to FIG. 5, the knee brace 10 is laid out flat with the leg of the user having the affected knee overlaying it. The edge 80 of the main body 20 of the sleeve 12 is drawn anteriorly across the lateral side of the leg and positioned on the anterior of the leg with the indentation 106 in the edge 80 of the main body 20 aligned around the patella of the affected knee. The upper and lower straps 56, 62 as well as the edge 82 of the main body 20 and tension tabs 26, 28, 30, 32 remain laid out posterior to the leg and extend in a medial direction from the leg. Referring additionally to FIG. 6, the upper inner tension tab 26 is drawn anteriorly across the medial side of the leg using the finger pull 108 and positioned on the anterior of the leg above the patella. The releasable fastener 100 on the inner face of the upper inner tension tab 26 is fastened to the cooperative releasable fastener on the outer face 72 of the main body 20 of the sleeve 12 on or proximal to the edge 80 (i.e., at the edge 80) and above the patella. Referring to FIG. 7, the lower inner tension tab 28 is similarly drawn anteriorly across the medial side of the leg using the finger pull 108 and positioned on the anterior of the leg below the patella with the indentation 102 in the outer edge 92 of the inner tab flap 88 aligned with the indentation 106 around the patella. The releasable fastener 100 on the inner face of the lower inner tension tab 28 is fastened to the cooperative releasable fastener on the outer face 72 of the main body 20 of the sleeve 12 on or proximal to the edge 80 (i.e., at the edge 80) and below the patella.

Figure 8:
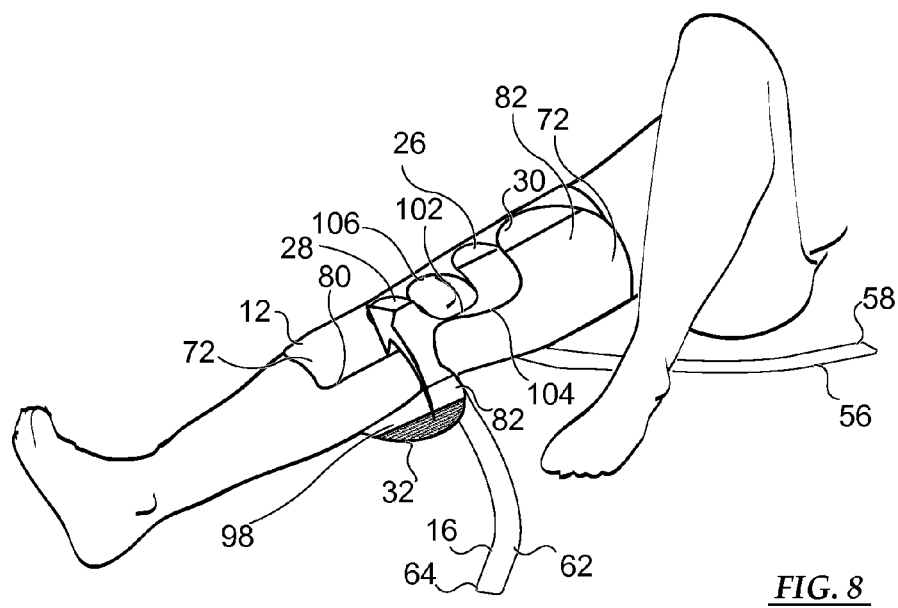
Figure 9:
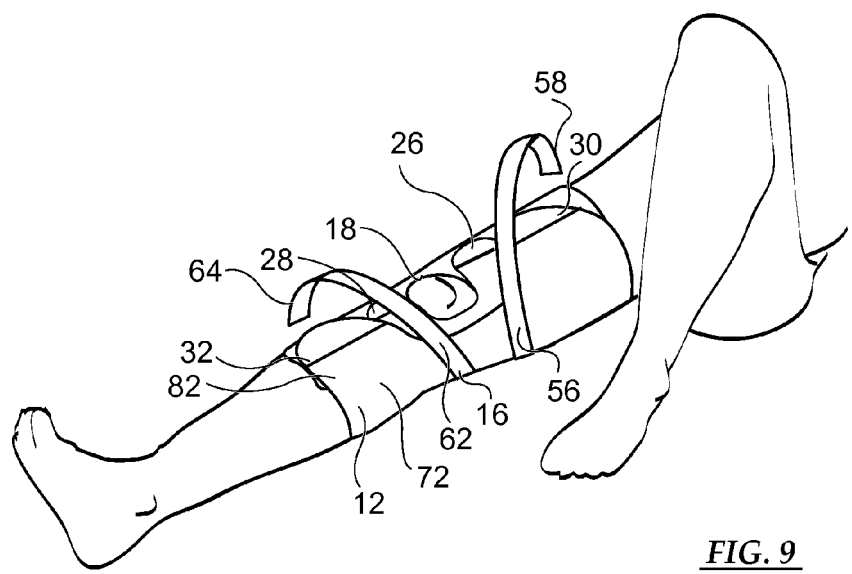

Referring to FIG. 8, the upper outer tension tab 30 is drawn anteriorly across the medial side of the leg using the finger pull 108 and positioned on the anterior of the leg above the patella and substantially above the upper inner tension tab 26 with the lower edge of the upper outer tension tab 30 overlapping the upper edge of the upper inner tension tab 26. The releasable fastener 100 on the inner face of the upper outer tension tab 30 is fastened to the cooperative releasable fastener on the outer face 72 of the main body 20 of the sleeve 12 on or proximal to the edge 80 (i.e., at the edge 80) and above the patella and upper inner tension tab 26. Referring to FIG. 9, the lower outer tension tab 32 is similarly drawn anteriorly across the medial side of the leg using the finger pull 108 and positioned on the anterior of the leg below the patella and substantially below the lower inner tension tab 28 with the upper edge of the lower outer tension tab 32 overlapping the lower edge of the lower inner tension tab 28. The releasable fastener 100 on the inner face of the lower outer tension tab 32 is fastened to the cooperative releasable fastener on the outer face 72 of the main body 20 of the sleeve 12 on or proximal to the edge 80 (i.e., at the edge 80) and below the patella and lower inner tension tab 28, thereby continuously joining the edges 80, 82 of the main body 20 and configuring the sleeve 12 in a tube-like manner. The indentation 104 in the edge 82 of the main body 20 is aligned with the indentations 102, 106 around the patella, thereby forming the patellar opening 18.

Figure 10:
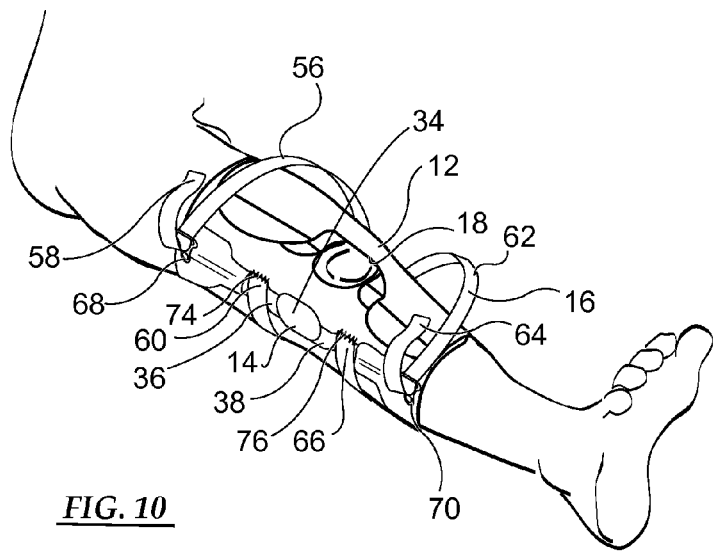
Figure 11:
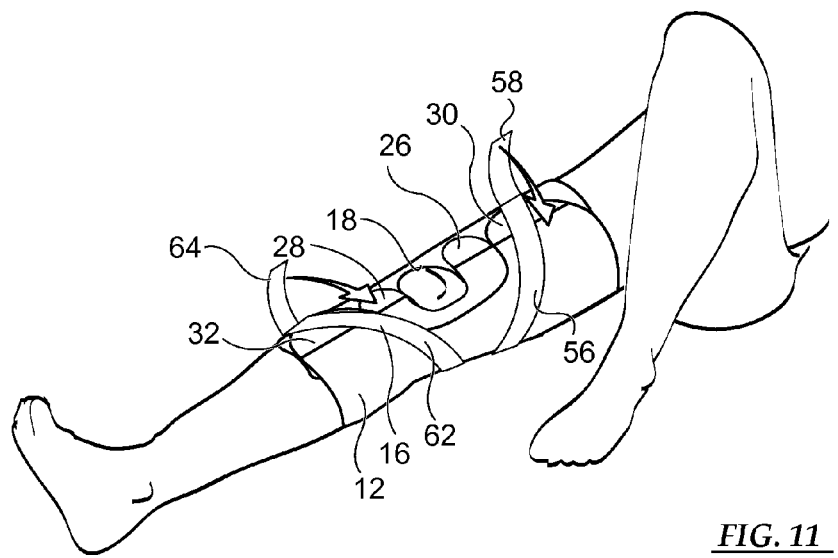

Referring additionally to FIGS. 10 and 11, the free first end 58 of the upper strap 56 is drawn diagonally upwardly and posteriorly from the fixed second end 60 of the upper strap 56 at the upper union 74 in sequence across the upper arm 40 and the lateral, posterior, medial and anterior sides of the leg to the upper strap retainer 68. The free first end 58 of the upper strap 56 is threaded through the strap loop of the upper strap retainer 68 and the free first end 58 is doubled back over the outer face of the upper strap 56 and releasably fastened thereto by means of the releasable fastener 78 to effect releasable attachment of the upper strap 56 to the upper cuff 42 at the upper strap retainer 68. The free first end 64 of the lower strap 62 is similarly drawn diagonally downwardly and posteriorly from the fixed second end 66 of the lower strap 62 at the lower union 76 in sequence across the lower arm 48 and the lateral, posterior, medial and anterior sides of the leg to the lower strap retainer 70. The free first end 64 of the lower strap 62 is threaded through the strap loop of the lower strap retainer 70 and the free first end 64 is doubled back over the outer face of the lower strap 62 and releasably fastened thereto by the releasable fastener 78 to effect releasable attachment of the lower strap 62 to the lower cuff 50 at the lower strap retainer 70.

The present strapping system 16 enables the user to adjust the length and correspondingly the tension of each strap 56, 62 by selection of the point on the outer face of each strap 56, 62 where the free first end 58, 64 of each strap 56, 62, respectively, is releasably fastened by fasteners 78. In particular, lengthening the upper strap 56, thereby loosening it and correspondingly untensioning it, is effected by releasably fastening the free first end 58 of the upper strap 56 to a point on the outer face of the upper strap 56 closer to the upper strap retainer 68. Shortening the upper strap 56, thereby tightening it and correspondingly tensioning it, is effected by releasably fastening the free first end 58 of the upper strap 56 to a point on the outer face of the upper strap 56 further from the upper strap retainer 68. Similarly, lengthening the lower strap 62, thereby loosening it and correspondingly untensioning it, is effected by releasably fastening the free first end 64 of the lower strap 62 to a point on the outer face of the lower strap 62 closer to the lower strap retainer 70. Shortening the lower strap 62, thereby tightening it and correspondingly tensioning it, is effected by releasably fastening the free first end 64 of the lower strap 62 to a point on the outer face of the lower strap 62 further from the lower strap retainer 70.

Although not shown, it is within the scope of the present invention to employ other alternatively-configured strap retainers known in the art or to omit the upper and lower strap retainers 68, 70 from the knee brace 10 altogether. In accordance with the alternate embodiment, wherein the upper and lower strap retainers 68, 70 are omitted from the knee brace 10, the free first ends 58, 64 of the upper and lower straps 56, 62, respectively, are releasably attached directly onto the outer face 72 of the sleeve 12 by means of the cooperative hook fasteners 78 on the first ends 58, 64 of the upper and lower straps 56, 62, respectively, and loop material covering or integrally forming the outer face 72 of the sleeve 12.

The specific configuration and characteristics of the above-described knee brace 10 achieve a number of functional advantages when the knee brace 10 is worn on the leg of a user. It is apparent that by shortening or lengthening the upper and lower straps 56, 62, correspondingly tensions or untensions them, respectively, the user is advantageously able to adjust the biasing force that the rotational hinge 34 applies to the knee. In particular, decreasing the length, thereby increasing the tension of the upper and lower straps 56, 62, increases the medially-directed force that the upper and lower straps 56, 62 apply to the longitudinal support assembly 14, which in turn increases the medial biasing force that the rotational hinge 34 applies to the knee of the user. Conversely, increasing the length, thereby decreasing the tension of the upper and lower straps 56, 62, decreases the medially-directed force that the upper and lower straps 56, 62 apply to the longitudinal support assembly 14, which in turn decreases the medial biasing force that the rotational hinge 34 applies to the knee of the user.

It is further noted that the upper and lower strap attachments 112, 114 advantageously function to focus the tensioning force of the upper and lower straps 56, 62 onto the longitudinal support assembly 14, in addition to advantageously functioning as strap guides which maintain the upper and lower straps 56, 62 in their desired pathway between the upper and lower unions 74, 76 and upper and lower strap retainers 68, 70, respectively. In sum, the specific configuration of the strapping system 16 and its spatial relation to the sleeve 12 and longitudinal support assembly 14 advantageously enables the user or a medical professional overseeing care of the user to carefully control the osteoarthritic treatment protocol and ultimately the overall treatment effectiveness of the knee brace 10.

Another advantageous function of the present knee brace 10 is the ability of the upper and lower inner tension tabs 26, 28 on the sleeve 12 to enhance the radial compression forces of the knee brace 10 against the leg of the user while simultaneously specifically focusing them onto the knee of the user where the forces are most effective for osteoarthritic treatment. The ability of the upper and lower outer tension tabs 30, 32 to further enhance the radial compression forces of the knee brace 10 against the leg of the user also makes a significant contribution to the overall effectiveness of the knee brace 10.

Figure 12:
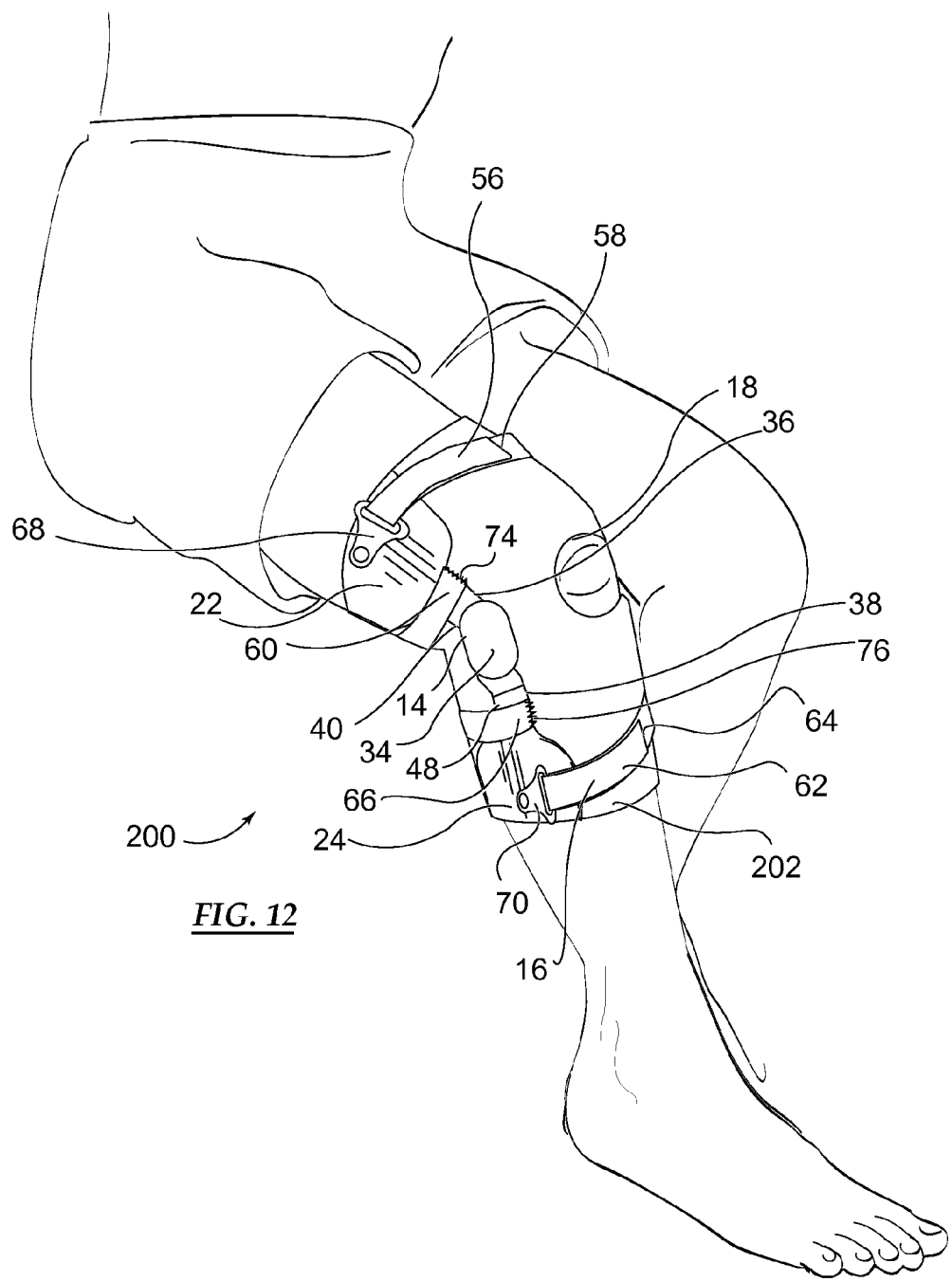
FIG. 12 is a perspective view of an alternate embodiment of an orthopedic knee brace of the present invention worn on the leg of a user.

Referring to FIG. 12, an alternate embodiment of an orthopedic knee brace of the present invention is shown worn on the leg of a user and generally designated 200. Like reference characters in FIG. 12 indicate the same or similar elements as in FIG. 1. The knee brace 200 of FIG. 12 preferably has substantially the same or similar longitudinal support assembly 14 and strapping system 16 as the knee brace 10 of FIG. 1. The knee brace 200 also has a sleeve 202 which may be fabricated from the same materials as the sleeve 12 of the knee brace 10. However, the knee brace 200 differs from the knee brace 10 in the configuration of the sleeve 202. Unlike the sleeve 12, the sleeve 202 has a substantially permanent tube-like configuration even when off the leg. As such, the sleeve 202 of the knee brace 200 is a unitary body with upper and lower cuff pockets 22, 24, but lacking the opposing vertical edges 80, 82 of the sleeve 12. The sleeve 202 further lacks the inner tab flap 88, upper and lower inner tension tabs 26, 28 and upper and lower outer tension tabs 30, 32 of the sleeve 12.

The knee brace 200 and correspondingly the sleeve 202 occupy substantially the same position on the leg of the user as the knee brace 10 and correspondingly the sleeve 12, i.e., over the knee and the adjacent portions of the upper and lower leg. However, the knee brace 200 is not mounted on the leg by wrapping the sleeve 202 around the leg in the manner of the knee brace 10 and sleeve 12 described above. Instead the knee brace 200 is mounted on the leg by simply placing the foot of the affected leg through the sleeve 202 and sliding the sleeve 202 up over the knee so that the patellar opening 18 of the sleeve 202 aligns with the patella and the longitudinal support assembly 14 is positioned alongside the lateral side of the leg with the rotational hinge 34 engaging the lateral side of the knee. The strapping system 16 is then fitted to the leg in substantially the same manner as described above with respect to the knee brace 10.

While the forgoing preferred embodiments of the invention have been described and shown, it is understood that alternatives and modifications, such as those suggested and others, may be made thereto and fall within the scope of the present invention. For example, the knee braces 10, 200 specifically described herein treat overloading of the medial compartment of the knee by positioning the longitudinal support assembly 14 on the lateral side of the leg to exert a biasing force on the knee in the medial direction which reduces the load on the medial compartment. However, it is within the scope of the present invention and readily within the purview of the ordinary artisan to employ the teaching herein to adapt the knee braces 10, 200 to treat overloading of the lateral compartment of the knee. In particular, the longitudinal support assembly 14 is positioned on the medial side of the leg while correspondingly reversing the position of the strapping system 16 to exert a biasing force on the knee in the lateral direction, thereby reducing the load on the lateral compartment. It is further within the scope of the present invention and readily within the purview of the ordinary artisan to reverse the position of the sleeve 12 of the knee brace 10 in correspondence with the longitudinal support assembly 14 so that the tension tabs 26, 28, 30, 32 extend in the medial direction across the anterior of the leg for anterior fastening when the position of the longitudinal support assembly 14 is reversed as described above. Additionally, the position of the sleeve 12 of the knee brace 10 can alternatively be reversed so that the tension tabs 26, 28, 30, 32 extend in the medial or lateral direction across the posterior of the leg for posterior fastening.

We claim:

1. A soft knee brace adapted to treat osteoarthritis by wearing the soft knee brace on a leg having anterior, posterior, lateral and medial sides and including an upper leg, a lower leg and a knee with a patella positioned on the anterior side of the leg at the knee and a knee condyle positioned at the lateral and medial sides of the leg at the knee, wherein the patella has a vertical length, a lateral side and a medial side and is horizontally bounded by an upper horizontal patellar edge and a lower horizontal patellar edge, the soft knee brace comprising:

a pliant compression sleeve having a pliant outer body, a pliant inner flap, an inoperative configuration and an operative configuration;

said pliant outer body comprises a body upper horizontal edge, a body lower horizontal edge, a body inner face, a body outer face, a body mid-section, a first vertical body edge, a second vertical body edge, a first body tension tab integral with said second vertical body edge and a second body tension tab integral with said second vertical body edge;

said pliant inner flap comprises a flap inner face, a flap outer face, a first vertical flap edge, a second vertical flap edge, a first flap tension tab integral with said second vertical flap edge and a second flap tension tab integral with said second vertical flap edge, wherein said first vertical flap edge is attached to said pliant outer body at an attachment union on said body inner face;

when said pliant compression sleeve is in said inoperative configuration, said pliant compression sleeve is adapted to be laid out off of the leg, said first vertical body edge and said second vertical body edge are positioned opposite one another vertically bounding said pliant outer body, said body mid-section is positioned midway between said first vertical body edge and said second vertical body edge, said first body tension tab and said second body tension tab extend in an extension direction away from said first vertical body edge, said first vertical flap edge and said second vertical flap edge are positioned opposite one another vertically bounding said pliant inner flap, said attachment union is positioned between said first vertical body edge and said second vertical body edge and proximal to said second vertical body edge and said first flap tension tab and said second flap tension tab extend in said extension direction; and when said pliant compression sleeve is in said operative configuration, said pliant outer body is adapted to wrap around and encircle the knee, the upper leg and the lower leg and engage the anterior side, the posterior side, the lateral side and the medial side of the leg about the knee with said body inner face adapted to face an inward direction toward the knee, said body outer face adapted to face an outward direction away from the knee and said body mid-section adapted to engage the posterior side of the leg, said first vertical body edge and said second vertical body edge are adapted to engage one another at the anterior side of the leg, said first body tension tab is adapted to extend past said first vertical body edge and fasten to said body outer face adjacent to said first vertical body edge at the anterior side of the leg above the patella, said second body tension tab is adapted to extend past said first vertical body edge and fasten to said body outer face adjacent to said first vertical body edge at the anterior side of the leg below the patella, said attachment union is adapted to be positioned on the lateral or medial side of the patella, said pliant inner flap is adapted to extend from said attachment union with said flap inner face in engagement with the knee condyle and said flap outer face in engagement with said body inner face and extend past said first vertical body edge to an opposite side of the patella from said attachment union, thereby focusing an enhanced radial compression force against the knee condyle in a direction toward the opposite side of the patella, said first flap tension tab is adapted to extend past said first vertical body edge along the upper horizontal patellar edge above the patella and fasten to said body outer face on the opposite side of the patella adjacent to said first vertical body edge and said first body tension tab and said second flap tension tab is adapted to extend past said first vertical body edge along the lower horizontal patellar edge below the patella and fasten to said body outer face at the anterior side of the leg on the opposite side of the patella adjacent to said first vertical body edge and said second body tension tab.

2. The soft knee brace of claim 1, wherein said first body tension tab has a first body tab fastener adapted to fasten said first body tension tab to said body outer face with said first body tension tab extending over said first vertical body edge and said second body tension tab has a second body tab fastener adapted to fasten said second body tension tab to said body outer face with said second body tension tab extending over said first vertical body edge when said pliant compression sleeve is in said operative configuration.

3. The soft knee brace of claim 1, wherein said first flap tension tab has a first flap tab fastener and said second flap tension tab has a second flap tab fastener and, wherein said first tab fastener is adapted to fasten said first flap tension tab to said body outer face and said second flap tab fastener is adapted to fasten said second flap tension tab to said body outer face when said pliant compression sleeve is in said operative configuration.

4. The soft knee brace of claim 1, wherein said second vertical flap edge is adapted to be positioned along the vertical length of the patella, said second flap tension tab is adapted to extend over said first vertical body edge and said first flap tension tab is adapted to extend over said first vertical body edge when said pliant compression sleeve is in said operative configuration.

5. The soft knee brace of claim 1, wherein said first vertical flap edge is beneath said pliant outer body and said second vertical flap edge extends out from beneath said second vertical body edge when said pliant compression sleeve is in said operative configuration.

6. The soft knee brace of claim 1, wherein said pliant outer body overlaps said pliant inner flap when said pliant compression sleeve is in said operative configuration.

7. The soft knee brace of claim 1, wherein said pliant inner flap is pivotable about said attachment union.

8. The soft knee brace of claim 1 further comprising a rigid or semi-rigid longitudinal support assembly engaging a longitudinal axis of said pliant outer body running between said body upper horizontal edge and said body lower horizontal edge, said longitudinal support assembly including an upper support member, a lower support member and a hinge rotatably connecting said upper support member and said lower support member, wherein said longitudinal support assembly is adapted to extend in a longitudinal position along the medial or lateral side of the leg termed a support member side when said pliant compression sleeve is in said operative configuration, and wherein said upper support member is positioned above said hinge, longitudinally positionable adjacent the upper leg on the support member side of the leg, said lower support member is positioned below said hinge, longitudinally positionable adjacent the lower leg on the support member side of the leg and said hinge is positionable adjacent the knee on the support member side of the leg.

9. The soft knee brace of claim 1, wherein said attachment union is adapted to continuously extend along the vertical length of the patella in its entirety when said pliant compression sleeve is in said operative configuration.

10. The soft knee brace of claim 1, wherein said first body tension tab fastens to said body outer face at a first body fastening point, said second body tension tab fastens to said body outer face at a second body fastening point, said first flap tension tab fastens to said body outer face at a second flap fastening point and said second flap tension tab fastens to said body outer face at a first flap fastening point, and wherein said first body fastening point is vertically aligned beneath said body upper horizontal edge more proximal to said body upper horizontal edge than said body lower horizontal edge, said second body fastening point is vertically aligned above said body lower horizontal edge more proximal to said body lower horizontal edge than said body upper horizontal edge between said first body fastening point and said body lower horizontal edge, said first flap fastening point is vertically aligned beneath said first body fastening point between said first body fastening point and said second body fastening point, and said second flap fastening point is vertically aligned above said second body fastening point between said first flap fastening point and said second body fastening point.

11. The soft knee brace of claim 1 further comprising an indentation in said second vertical body edge between said first body tension tab and said second body tension tab to form at least in part a patellar opening in said pliant outer body adapted to receive the patella of the knee when said pliant compression sleeve is in said operative configuration.

12. The soft knee brace of claim 1, wherein said first body tension tab is vertically aligned beneath said body upper horizontal edge more proximal to said body upper horizontal edge than said body lower horizontal edge, said second body tension tab is vertically aligned above said body lower horizontal edge more proximal to said body lower horizontal edge than said body upper horizontal edge between said first body tension tab and said body lower horizontal edge, said first flap tension tab is vertically aligned beneath said first body tension tab between said first body tension tab and said second body tension tab, said first body tension tab overlaps said first flap tension tab, and said second flap tension tab is vertically aligned above said second body tension tab between said first flap tension tab and said second body tension tab when said pliant compression sleeve is in said inoperative configuration; and said first body tension tab overlaps said first flap tension tab and said second body tension tab overlaps said second flap tension tab when said pliant compression sleeve is in said operative configuration.

13. The soft knee brace of claim 12, wherein said first vertical flap edge is beneath said pliant outer body and said second vertical flap edge extends out from beneath said second vertical body edge when said pliant compression sleeve is in said operative configuration.

14. The soft knee brace of claim 13 further comprising an indentation in said second vertical body edge between said first body tension tab and said second body tension tab to form at least in part a patellar opening in said pliant outer body adapted to receive the patella of the knee when said pliant compression sleeve is in said operative configuration.

15. A soft knee brace adapted to treat osteoarthritis by wearing the soft knee brace on a leg having anterior, posterior, lateral and medial sides and including an upper leg, a lower leg and a knee with a patella positioned on the anterior side of the leg at the knee and a knee condyle positioned at the lateral and medial sides of the leg at the knee, wherein the patella has a vertical length, a lateral side and a medial side and is horizontally bounded by an upper horizontal patellar edge and a lower horizontal patellar edge, the soft knee brace comprising:

a pliant compression sleeve having a pliant outer body, a pliant inner body, an inoperative configuration and an operative configuration, wherein said pliant outer body has a body upper horizontal edge, a body lower horizontal edge, a first vertical body edge, a second vertical body edge, a body inner face, a body outer face, a body mid-section, a first body tension tab integral with said second vertical body edge and a second body tension tab integral with said second vertical body edge, wherein said pliant inner flap has a first vertical flap edge, a second vertical flap edge, a flap inner face, a flap outer face, a first flap tension tab integral with said second vertical flap edge and a second flap tension tab integral with said second vertical flap edge and, wherein said first vertical flap edge is attached to said pliant outer body at an attachment union on said body inner face;

when said pliant compression sleeve is in said inoperative configuration, said pliant compression sleeve is adapted to be laid out off of the leg, said first vertical body edge and said second vertical body edge are positioned opposite one another vertically bounding said pliant outer body, said body mid-section is positioned midway between said first vertical body edge and said second vertical body edge, said first body tension tab and said second body tension tab extend in an extension direction away from said first vertical body edge, said first vertical flap edge and said second vertical flap edge are positioned opposite one another vertically bounding said pliant inner flap, said attachment union is positioned between said first vertical body edge and said second vertical body edge and proximal to said second vertical body edge and said first flap tension tab and said second flap tension tab extend in said extension direction;

when said pliant compression sleeve is in said operative configuration, said pliant outer body is adapted to wrap around and encircle the knee, the upper leg and the lower leg and engage the anterior side, the posterior side, the lateral side and the medial side of the leg about the knee with said body inner face adapted to face an inward direction toward the knee, said body outer face adapted to face an outward direction away from the knee and said body mid-section adapted to engage the posterior side of the leg, said pliant outer body, said first vertical body edge and said second vertical body edge are adapted to engage one another at the anterior side of the leg, said first body tension tab is adapted to extend past said first vertical body edge and fasten to said body outer face adjacent to said first vertical body edge at the anterior side of the leg above the patella, said second body tension tab is adapted to extend past said first vertical body edge and fasten to said body outer face adjacent to said first vertical body edge at the anterior side of the leg below the patella, said attachment union is adapted to be positioned on the lateral or medial side of the patella, said pliant inner flap is adapted to extend in engagement with the knee condyle from said attachment union to an opposite side of the patella from said attachment union, thereby focusing an enhanced radial compression force against the knee condyle in a direction toward the opposite side of the patella, said first flap tension tab is adapted to extend past said first vertical body edge along the upper horizontal patellar edge above the patella and fasten to said body outer face at the anterior side of the leg on the opposite side of the patella adjacent to said first vertical body edge and said first body tension tab and said second flap tension tab is adapted to extend past said first vertical body edge along the lower horizontal patellar edge below the patella and fasten to said body outer face at the anterior side of the leg on the opposite side of the patella adjacent to said first vertical body edge and said second body tension tab;

a rigid or semi-rigid longitudinal support assembly including an upper support member, a lower support member and a hinge rotatably connecting said upper support member and said lower support member, wherein said longitudinal support assembly engages said pliant outer body and is adapted to extend in a longitudinal position along the medial or lateral side of the leg termed a support member side when said pliant compression sleeve is in said operative configuration, and wherein said upper support member is positioned above said hinge, longitudinally positionable adjacent the upper leg on the support member side of the leg, said lower support member is positioned below said hinge, longitudinally positionable adjacent the lower leg on the support member side of the leg and said hinge is positionable adjacent the knee on the support member side of the leg;

an upper strap having a second upper strap end positioned above said hinge, a first upper strap end positioned above said hinge and above said second upper strap end, a first upper strap longitudinal edge continuously extending from said first upper strap end to said second upper strap end, a second upper strap longitudinal edge continuously extending from said first upper strap end to said second upper strap end in parallel correspondence with said first upper strap longitudinal edge and an upper strap longitudinal axis defined by a centerline between said first upper strap longitudinal edge and said second upper strap longitudinal edge continuously extending from said first upper strap end to said second upper strap end, wherein said second upper strap end engages an upper engagement point on said upper support member proximal to said hinge and said upper strap extends from said upper engagement point to an upper connection point on said upper support member distal from and above said hinge and above said upper engagement point adjacent to a body upper horizontal edge of said pliant outer body where said first upper strap end is connected to said upper support member, wherein said upper strap is adapted to extend around the anterior side and the posterior side of the leg on the upper leg and around the medial or lateral side of the leg on the upper leg that is on a side of the leg opposite the support member side and is termed an opposite side, and wherein said upper strap longitudinal axis follows a helical operative path from said upper engagement point to said upper connection point and said upper strap longitudinal axis maintains a continuous line of contact with said pliant outer body where said pliant outer body engages the anterior side, the posterior side, and the opposite side of the leg on the upper leg when said pliant compression sleeve is in said operative configuration;

wherein said upper strap is adapted as a result of said helical operative path of said upper strap longitudinal axis to apply an upper biasing force to the support member side of the leg on the upper leg in a direction of the opposite side of the leg, and wherein no additional upper strap is provided to apply an upper counter force to the opposite side of the leg in a direction of the support member side of the leg on the upper leg that would cancel said upper biasing force, thereby enabling said upper biasing force to unload a compartment of the knee on the opposite side of the leg; and a lower strap positioned below said hinge and having a second lower strap end, a first lower strap end positioned below said second lower strap end, a first lower strap longitudinal edge continuously extending from said first lower strap end to said second lower strap end, a second lower strap longitudinal edge continuously extending from said first lower strap end to said second lower strap end in parallel correspondence with said first lower strap longitudinal edge and a lower strap longitudinal axis defined by a centerline between said first lower strap longitudinal edge and said second lower strap longitudinal edge continuously extending from said first lower strap end to said second lower strap end, wherein said second lower strap end engages a lower engagement point on said lower support member proximal to said hinge and said lower strap extends from said lower engagement point to a lower connection point on said lower support member distal from and below said hinge and below said lower engagement point adjacent to a body lower horizontal edge of said pliant outer body where said first lower strap end is connected to said lower support member, wherein said lower strap is adapted to extend around the anterior side and the posterior side of the leg on the lower leg and around the opposite side of the leg on the lower leg, and wherein said lower strap longitudinal axis follows a helical operative path from said lower engagement point to said lower connection point and said lower strap longitudinal axis maintains a continuous line of contact with said pliant outer body where said pliant outer body engages the anterior side, the posterior side, and the opposite side of the leg on the lower leg when said pliant compression sleeve is in said operative configuration;

wherein said lower strap is adapted as a result of said helical operative path of said lower strap longitudinal axis to apply a lower biasing force to the support member side of the leg on the lower leg in a direction of the opposite side of the leg, and wherein no additional lower strap is provided to apply a lower counter force to the opposite side of the leg on the lower leg in a direction of the support member side of the leg that would cancel said lower biasing force, thereby enabling said lower biasing force to unload the compartment of the knee on the opposite side of the leg.

16. The soft knee brace of claim 15, wherein said second upper strap end is attached to said pliant outer body adjacent to said upper engagement point.

17. The soft knee brace of claim 15, wherein connection of said first upper strap end to said upper connection point is effected by threading said first upper strap end through an upper strap retainer mounted on said upper support member at said upper connection point.

18. The soft knee brace of claim 15, wherein said second lower strap end is attached to said pliant outer body adjacent to said lower engagement point.

19. The soft knee brace of claim 15, wherein connection of said first lower strap end to said lower connection point is effected by threading said first lower strap end through a lower strap retainer mounted on said lower support member at said lower connection point.

20. The soft knee brace of claim 15, wherein said upper strap and said pliant outer body are adapted to extend around the opposite side of the leg on the upper leg when said pliant compression sleeve is in said operative configuration and said upper strap is free from attachment to said pliant outer body where said pliant outer body is adapted to extend around the opposite side of the leg on the upper leg.

21. The soft knee brace of claim 15, wherein said lower strap and said pliant outer body are adapted to extend around the opposite side of the leg on the lower leg when said pliant compression sleeve is in said operative configuration and said lower strap is free from attachment to said pliant outer body where said pliant outer body is adapted to extend around the opposite side of the leg on the lower leg.

22. A soft knee brace adapted to treat osteoarthritis by wearing the soft knee brace on a leg having anterior, posterior, lateral and medial sides and including an upper leg, a lower leg and a knee with a patella positioned on the anterior side of the leg at the knee and a knee condyle positioned at the lateral and medial sides of the leg at the knee, wherein the patella has a vertical length, a lateral side and a medial side and is horizontally bounded by an upper horizontal patellar edge and a lower horizontal patellar edge, the soft knee brace comprising:
  a pliant compression sleeve having a pliant outer body, a pliant inner flap, an inoperative configuration and an operative configuration;
  said pliant outer body comprises a body upper horizontal edge, a body lower horizontal edge, a body inner face, a body outer face, a body mid-section, a first vertical body edge, a second vertical body edge, a first body tension tab integral with said second vertical body edge and a second body tension tab integral with said second vertical body edge;
  said pliant inner flap comprises a flap inner face, a flap outer face, a first vertical flap edge, a second vertical flap edge, a first flap tension tab integral with said second vertical flap edge and a second flap tension tab integral with said second vertical flap edge, wherein said first vertical flap edge is attached to said pliant outer body at an attachment union on said body inner face;
  when said pliant compression sleeve is in said inoperative configuration, said pliant compression sleeve is adapted to be laid out off of the leg, said first vertical body edge and said second vertical body edge are positioned opposite one another vertically bounding said pliant outer body, said body mid-section is positioned midway between said first vertical body edge and said second vertical body edge, said first body tension tab and said second body tension tab extend in an extension direction away from said first vertical body edge, said first vertical flap edge and said second vertical flap edge are positioned opposite one another vertically bounding said pliant inner flap, said attachment union is positioned between said first vertical body edge and second vertical body edge and proximal to said second vertical body edge and said first flap tension tab and said second flap tension tab extend in said extension direction;
  when said pliant compression sleeve is in said operative configuration, said pliant outer body is adapted to wrap around and encircle the knee, the upper leg and the lower leg and engage the anterior side, the posterior side, the lateral side and the medial side of the leg about the knee with said body inner face adapted to face an inward direction toward the knee, said body outer face adapted to face an outward direction away from the knee and said body mid-section adapted to engage the posterior side of the leg, said first vertical body edge and said second vertical body edge are adapted to engage one another at the anterior side of the leg, said first body tension tab is adapted to extend past said first vertical body edge and fasten to said body outer face adjacent to said first vertical body edge at the anterior side of the leg above the patella, said second body tension tab is adapted to extend past said first vertical body edge and fasten to said body outer face adjacent to said first vertical body edge at the anterior side of the leg below the patella, said attachment union is adapted to be positioned on the lateral or medial side of the patella, said pliant inner flap is adapted to extend from said attachment union with said flap inner face in engagement with the knee condyle and said flap outer face in engagement with said body inner face and extend past said first vertical body edge to an opposite side of the patella from said attachment union, thereby focusing an enhanced radial compression force against the knee condyle in a direction toward the opposite side of the patella, said first flap tension tab is adapted to extend past said first vertical body edge along the upper horizontal patellar edge above the patella and fasten to said body outer face on the opposite side of the patella adjacent to said first vertical body edge and said first body tension tab and said second flap tension tab is adapted to extend past said first vertical body edge along the lower horizontal patellar edge below the patella and fasten to said body outer face at the anterior side of the leg on the opposite side of the patella adjacent to said first vertical body edge and said second body tension tab; and
  a rigid or semi-rigid longitudinal support assembly including an upper support member, a lower support member and a hinge rotatably connecting said upper support member and said lower support member, wherein said longitudinal support assembly engages said pliant outer body and is adapted to extend in a longitudinal position along the medial or lateral side of the leg termed a support member side when said pliant compression sleeve is in said operative configuration, and wherein said upper support member is positioned above said hinge, longitudinally positionable adjacent the upper leg on the support member side of the leg, said lower support member is positioned below said hinge, longitudinally positionable adjacent the lower leg on the support member side of the leg and said hinge is positionable adjacent the knee on the support member side of the leg.

23. The soft knee brace of claim 22 further comprising an upper strap having a second upper strap end positioned above said hinge, a first upper strap end positioned above said hinge and above said second upper strap end, a first upper strap longitudinal edge continuously extending from said first upper strap end to said second upper strap end, a second upper strap longitudinal edge continuously extending from said first upper strap end to said second upper strap end in parallel correspondence with said first upper strap longitudinal edge and an upper strap longitudinal axis defined by a centerline between said first upper strap longitudinal edge and said second upper strap longitudinal edge continuously extending from said first upper strap end to said second upper strap end, wherein said second upper strap end engages an upper engagement point on said upper support member proximal to said hinge and said upper strap extends from said upper engagement point to an upper connection point on said upper support member distal from and above said hinge and above said upper engagement point adjacent to said body upper horizontal edge where said first upper strap end is connected to said upper support member, wherein said upper strap is adapted to extend around the anterior side and the posterior side of the leg on the upper leg and around the medial or lateral side of the leg on the upper leg that is a side of the leg opposite the support member side and is termed an opposite side, and wherein said upper strap longitudinal axis follows a helical operative path from said upper engagement point to said upper connection point and said upper strap longitudinal axis maintains a continuous line of contact with said pliant outer body where said pliant outer body engages the anterior side, the posterior side, and the opposite side of the leg on the upper leg when said pliant compression sleeve is in said operative configuration.

24. The knee brace of claim 23, wherein said upper strap is adapted as a result of said helical operative path of said upper strap longitudinal axis to apply an upper biasing force to the support member side of the leg on the upper leg in a direction of the opposite side of the leg, and wherein no additional upper strap is provided to apply an upper counter force to the opposite side of the leg in a direction of the support member side of the leg on the upper leg that would cancel said upper biasing force, thereby enabling said upper biasing force to unload a compartment of the knee on the opposite side of the leg.

25. The soft knee brace of claim 22 further comprising a lower strap positioned below said hinge and having a second lower strap end, a first lower strap end positioned below said second lower strap end, a first lower strap longitudinal edge continuously extending from said first lower strap end to said second lower strap end, a second lower strap longitudinal edge continuously extending from said first lower strap end to said second lower strap end in parallel correspondence with said first lower strap longitudinal edge and a lower strap longitudinal axis defined by a centerline between said first lower strap longitudinal edge and said second lower strap longitudinal edge continuously extending from said first lower strap end to said second lower strap end, wherein said second lower strap end engages a lower engagement point on said lower support member proximal to said hinge and said lower strap extends from said lower engagement point to a lower connection point on said lower support member distal from and below said hinge and below said lower engagement point adjacent to said body lower horizontal edge where said first lower strap end is connected to said lower support member, wherein said lower strap is adapted to extend around the anterior side, the posterior side and the opposite side of the leg on the lower leg, and wherein said lower strap longitudinal axis follows a helical operative path from said lower engagement point to said lower connection point and said lower strap longitudinal axis maintains a continuous line of contact with said pliant outer body where said pliant outer body engages the anterior side, the posterior side, and the opposite side of the leg on the lower leg when said pliant compression sleeve is in said operative configuration.

26. The soft knee brace of claim 25, wherein said lower strap is adapted as a result of said helical operative path of said lower strap longitudinal axis to apply a lower biasing force to the support member side of the leg on the lower leg in a direction of the opposite side of the leg, and wherein no additional lower strap is provided to apply a lower counter force to the opposite side of the leg on the lower leg in a direction of the support member side of the leg that would cancel said lower biasing force, thereby enabling said lower biasing force to unload the compartment of the knee on the opposite side of the leg.

27. A soft knee brace adapted to treat osteoarthritis by wearing the soft knee brace on a leg having anterior, posterior, lateral and medial sides and including an upper leg, a lower leg and a knee with a patella positioned on the anterior side of the leg at the knee and a knee condyle positioned at the lateral and medial sides of the leg at the knee, wherein the patella has a vertical length, a lateral side and a medial side and is horizontally bounded by an upper horizontal patellar edge and a lower horizontal patellar edge, the soft knee brace comprising:

a pliant compression sleeve having a pliant outer body, a pliant inner flap, an inoperative configuration and an operative configuration;

said pliant outer body comprises a body upper horizontal edge, a body lower horizontal edge, a body inner face, a body outer face, a body mid-section, a first vertical body edge, a second vertical body edge, a first body tension tab integral with said second vertical body edge and a second body tension tab integral with said second vertical body edge;

said pliant inner flap comprises a flap inner face, a flap outer face, a first vertical flap edge, a second vertical flap edge, a first flap tension tab integral with said second vertical flap edge and a second flap tension tab integral with said second vertical flap edge, wherein said first vertical flap edge is attached to said pliant outer body at an attachment union on said body inner face;

when said pliant compression sleeve is in said inoperative configuration, said pliant compression sleeve is adapted to be laid out off of the leg, said first vertical body edge and said second vertical body edge are positioned opposite one another vertically bounding said pliant outer body, said body mid-section is positioned midway between said first vertical body edge and said second vertical body edge, said first body tension tab and said second body tension tab extend in an extension direction away from said first vertical body edge, said first vertical flap edge and said second vertical flap edge are positioned opposite one another vertically bounding said pliant inner flap, said attachment union is positioned between said first vertical body edge and said second vertical body edge and proximal to said second vertical body edge and said first flap tension tab and said second flap tension tab extend in said extension direction;

when said pliant compression sleeve is in said operative configuration, said pliant outer body is adapted to wrap around and encircle the knee, the upper leg and the lower leg and engage the anterior side, the posterior side, the lateral side and the medial side of the leg about the knee with said body inner face adapted to face an inward direction toward the knee, said body outer face adapted to face an outward direction away from the knee and said body mid-section adapted to engage the posterior side of the leg, said first vertical body edge and said second vertical body edge are adapted to engage one another at the anterior side of the leg, said first body tension tab is adapted to extend past said first vertical body edge and fasten to said body outer face adjacent to said first vertical body edge at the anterior side of the leg above the patella, said second body tension tab is adapted to extend past said first vertical body edge and fasten to said body outer face adjacent to said first vertical body edge at the anterior side of the leg below the patella, said attachment union is adapted to be positioned on the lateral or medial side of the patella, said pliant inner flap is adapted to extend from said attachment union with said flap inner face in engagement with the knee condyle and said flap outer face in engagement with said body inner face and extend past said first vertical body edge to an opposite side of the patella from said attachment union, thereby focusing an enhanced radial compression force against the knee condyle in a direction toward the opposite side of the patella, said first flap tension tab is adapted to extend past said first vertical body edge along the upper horizontal patellar edge above the patella and fasten to said body outer face on the opposite side of the patella adjacent to said first vertical body edge and said first body tension tab and said second flap tension tab is adapted to extend past said first vertical body edge along the lower horizontal patellar edge below the patella and fasten to said body outer face at the anterior side of the leg on the opposite side of the patella adjacent to said first vertical body edge and said second body tension tab; and an upper strap adapted to extend around the upper leg and engage said pliant outer body when said pliant compression sleeve is in said operative configuration.

28. A soft knee brace adapted to treat osteoarthritis by wearing the soft knee brace on a leg having anterior, posterior, lateral and medial sides and including an upper leg, a lower leg and a knee with a patella positioned on the anterior side of the leg at the knee and a knee condyle positioned at the lateral and medial sides of the leg at the knee, wherein the patella has a vertical length, a lateral side and a medial side and is horizontally bounded by an upper horizontal patellar edge and a lower horizontal patellar edge, the soft knee brace comprising:

a pliant compression sleeve having a pliant outer body, a pliant inner flap, an inoperative configuration and an operative configuration;

said pliant outer body comprises a body upper horizontal edge, a body lower horizontal edge, a body inner face, a body outer face, a body mid-section, a first vertical body edge, a second vertical body edge, a first body tension tab integral with said second vertical body edge and a second body tension tab integral with said second vertical body edge;

said pliant inner flap comprises a flap inner face, a flap outer face, a first vertical flap edge, a second vertical flap edge, a first flap tension tab integral with said second vertical flap edge and a second flap tension tab integral with said second vertical flap edge, wherein said first vertical flap edge is attached to said pliant outer body at an attachment union on said body inner face;

when said pliant compression sleeve is in said inoperative configuration, said pliant compression sleeve is adapted to be laid out off of the leg, said first vertical body edge and said second vertical body edge are positioned opposite one another vertically bounding said pliant outer body, said body mid-section is positioned midway between said first vertical body edge and said second vertical body edge, said first body tension tab and said second body tension tab extend in an extension direction away from said first vertical body edge, said first vertical flap edge and said second vertical flap edge are positioned opposite one another vertically bounding said pliant inner flap, said attachment union is positioned between said first vertical body edge and said second vertical body edge and proximal to said second vertical body edge and said first flap tension tab and said second flap tension tab extend in said extension direction;

when said pliant compression sleeve is in said operative configuration, said pliant outer body is adapted to wrap around and encircle the knee, the upper leg and the lower leg and engage the anterior side, the posterior side, the lateral side and the medial side of the leg about the knee with said body inner face adapted to face an inward direction toward the knee, said body outer face adapted to face an outward direction away from the knee and said body mid-section adapted to engage the posterior side of the leg, said first vertical body edge and said second vertical body edge are adapted to engage one another at the anterior side of the leg, said first body tension tab is adapted to extend past said first vertical body edge and fasten to said body outer face adjacent to said first vertical body edge at the anterior side of the leg above the patella, said second body tension tab is adapted to extend past said first vertical body edge and fasten to said body outer face adjacent to said first vertical body edge at the anterior side of the leg below the patella, said attachment union is adapted to be positioned on the lateral or medial side of the patella, said pliant inner flap is adapted to extend from said attachment union with said flap inner face in engagement with the knee condyle and said flap outer face in engagement with said body inner face and extend past said first vertical body edge to an opposite side of the patella from said attachment union, thereby focusing an enhanced radial compression force against the knee condyle in a direction toward the opposite side of the patella, said first flap tension tab is adapted to extend past said first vertical body edge along the upper horizontal patellar edge above the patella and fasten to said body outer face on the opposite side of the patella adjacent to said first vertical body edge and said first body tension tab and said second flap tension tab is adapted to extend past said first vertical body edge along the lower horizontal patellar edge below the patella and fasten to said body outer face at the anterior side of the leg on the opposite side of the patella adjacent to said first vertical body edge and said second body tension tab; and a lower strap adapted to extend around the lower leg and engage said pliant outer body when said pliant compression sleeve is in said operative configuration.

29. A soft knee brace adapted to treat osteoarthritis by wearing the soft knee brace on a leg having anterior, posterior, lateral and medial sides and including an upper leg, a lower leg and a knee with a patella positioned on the anterior side of the leg at the knee and a knee condyle positioned at the lateral and medial sides of the leg at the knee, wherein the patella has a vertical length, a lateral side and a medial side and is horizontally bounded by an upper horizontal patellar edge and a lower horizontal patellar edge, the soft knee brace comprising:

a pliant compression sleeve having a pliant outer body, a pliant inner flap, an inoperative configuration and an operative configuration;

said pliant outer body comprises a body upper horizontal edge, a body lower horizontal edge, a body inner face, a body outer face, a body mid-section, a first vertical body edge, a second vertical body edge, a first body tension tab integral with said second vertical body edge and a second body tension tab integral with said second vertical body edge;

said pliant inner flap comprises a flap inner face, a flap outer face, a first vertical flap edge, a second vertical flap edge, a first flap tension tab integral with said second vertical flap edge and a second flap tension tab integral with said second vertical flap edge, wherein said first vertical flap edge is attached to said pliant outer body at an attachment union on said body inner face;

when said pliant compression sleeve is in said inoperative configuration, said pliant compression sleeve is adapted to be laid out off of the leg, said first vertical body edge and said second vertical body edge are positioned opposite one another vertically bounding said pliant outer body, said body mid-section is positioned midway between said first vertical body edge and said second vertical body edge, said first body tension tab and said second body tension tab extend in an extension direction away from said first vertical body edge, said first vertical flap edge and said second vertical flap edge are positioned opposite one another vertically bounding said pliant inner flap, said attachment union is positioned between said first vertical body edge and said second vertical body edge and proximal to said second vertical body edge and said first flap tension tab and said second flap tension tab extend in said extension direction;

when said pliant compression sleeve is in said operative configuration, said pliant outer body is adapted to wrap around and encircle the knee, the upper leg and the lower leg and engage the anterior side, the posterior side, the lateral side and the medial side of the leg about the knee with said body inner face adapted to face an inward direction toward the knee, said body outer face adapted to face an outward direction away from the knee and said body mid-section adapted to engage the posterior side of the leg, said first vertical body edge and said second vertical body edge are adapted to engage one another at the anterior side of the leg, said first body tension tab is adapted to extend past said first vertical body edge and fasten to said body outer face adjacent to said first vertical body edge at the anterior side of the leg above the patella, said second body tension tab is adapted to extend past said first vertical body edge and fasten to said body outer face adjacent to said first vertical body edge at the anterior side of the leg below the patella, said attachment union is adapted to be positioned on the lateral or medial side of the patella, said pliant inner flap is adapted to extend from said attachment union with said flap inner face in engagement with the knee condyle and said flap outer face in engagement with said body inner face and extend past said first vertical body edge to an opposite side of the patella from said attachment union, thereby focusing an enhanced radial compression force against the knee condyle in a direction toward the opposite side of the patella, said first flap tension tab is adapted to extend past said first vertical body edge along the upper horizontal patellar edge above the patella and fasten to said body outer face on the opposite side of the patella adjacent to said first vertical body edge and said first body tension tab and said second flap tension tab is adapted to extend past said first vertical body edge along the lower horizontal patellar edge below the patella and fasten to said body outer face at the anterior side of the leg on the opposite side of the patella adjacent to said first vertical body edge and said second body tension tab;

a lower strap adapted to extend around the lower leg and engage said pliant outer body when said pliant compression sleeve is in said operative configuration; and an upper strap adapted to extend around the upper leg and engage said pliant outer body when said pliant compression sleeve is in said operative configuration.

30. The soft knee brace of claim 29 further comprising a rigid or semi-rigid longitudinal support assembly including an upper support member, a lower support member and a hinge rotatably connecting said upper support member and said lower support member, wherein said longitudinal support assembly engages said pliant outer body and is adapted to extend in a longitudinal position along the medial or lateral side of the leg termed a support member side when said pliant compression sleeve is in said operative configuration, and wherein said upper support member is positioned above said hinge, longitudinally positionable adjacent the upper leg on the support member side of the leg, said lower support member is positioned below said hinge, longitudinally positionable adjacent the lower leg on the support member side of the leg and said hinge is positionable adjacent the knee on the support member side of the leg.

* * * * *